United States Patent [19]

Brown et al.

[11] Patent Number: 5,153,227

[45] Date of Patent: Oct. 6, 1992

[54] PHENYLSULFONYL NITROMETHANES AS ALDOSE REDUCTASE INHIBITORS

[75] Inventors: Steven P. Brown; Anthony L. Cooper, both of Bude; Jethro L. Longridge, Macclesfield; Jeffrey J. Morris, Sandbach; John Preston, Knutsford, all of England

[73] Assignee: Imperial Chemical Industries PLC, London, England

[21] Appl. No.: 306,676

[22] Filed: Feb. 6, 1989

Related U.S. Application Data

[63] Continuation-in-part of Ser. No. 229,523, Aug. 8, 1988, abandoned.

[30] Foreign Application Priority Data

Aug. 6, 1987 [GB] United Kingdom ............... 8718619
Apr. 7, 1988 [GB] United Kingdom ............. 8808117-9

[51] Int. Cl.$^5$ .................... C07C 317/26; A61K 31/13
[52] U.S. Cl. ................................. 514/646; 514/450; 514/452; 514/466; 514/510; 514/524; 514/538; 514/568; 514/569; 514/585; 514/603; 514/604; 514/605; 514/617; 514/618; 514/629; 514/656; 514/657; 514/709; 514/710; 549/348; 549/349; 549/350; 549/358; 549/359; 549/366; 549/432; 549/433; 549/443; 558/413; 560/10; 560/12; 560/24; 560/28; 562/427; 562/430; 564/85; 564/92; 564/99; 564/162; 564/184; 564/218; 564/222; 564/427; 564/428; 564/440; 568/29; 568/30
[58] Field of Search ................ 564/440, 218, 162, 85, 564/99, 184, 92; 514/648, 709, 710, 629, 618, 603, 485, 605, 604, 617; 568/30; 560/24

[56] References Cited

U.S. PATENT DOCUMENTS

| | | | |
|---|---|---|---|
| 3,882,247 | 5/1975 | Bullock | 514/709 |
| 4,053,633 | 10/1977 | Goralski et al. | 568/30 |
| 4,567,004 | 1/1986 | Blank et al. | 568/30 |

FOREIGN PATENT DOCUMENTS

| | | | |
|---|---|---|---|
| 8269 | 2/1980 | European Pat. Off. | 514/709 |
| 479761 | 5/1976 | U.S.S.R. | 568/30 |

OTHER PUBLICATIONS

*J. Chem. Soc.*, Chemical Communications, 1984, 670.
*J. Organic Chemistry*, 1978, 43, 3101.
*J. Chem. Soc.*, Chemical Communications, 1978, 362.
*J. Organic Chemistry*, 1986, 51, 1012–1015.
*Chemical Abstracts*, vol. 104, Abstract No. 168055 (1986).
*J. Prakt. Chem.*, 1920, 101, 136–137.
*Rec. Trav. Chim. Pays Bas*, 1974, 93, 11–14.
*Chemical Abstracts*, vol. 59, Abstract No. 6341g (1963).
*J. Polymer Science.* Polymer Chemistry Edition, 1985, 23, 1963–1972.
*J. Heterocyclic Chemistry*, 1977, 14, 1415–1416.
*Chemical Abstracts*, vol. 15, pp. 1013–1014 (1921).
STN Printout, 9th Collective Index, Aug. 1978.

*Primary Examiner*—Richard L. Raymond
*Assistant Examiner*—Scott C. Rand
*Attorney, Agent, or Firm*—Cushman, Darby & Cushman

[57] ABSTRACT

The invention concerns novel pharmaceutical compositions for use in the treatment of certain complications of diabetes and galactosemia and which contain a nitromethane derivative (or its non-toxic salt) as active ingredient. The nitromethane derivatives are inhibitors of the enzyme aldose reductase. Many of the inhibitors are novel and are provided, together with processes for their manufacture and use, as further features of the invention.

14 Claims, No Drawings

PHENYLSULFONYL NITROMETHANES AS ALDOSE REDUCTASE INHIBITORS

This application is a continuation-in-part of Ser. No. 07/229,523 filed Aug. 8, 1988 now abandoned.

This invention concerns novel pharmaceutical compositions containing a nitromethane derivative which is an inhibitor of the enzyme aldose reductase and which compositions are of value, for example, in the treatment of certain peripheral effects of diabetes or galactosemia. A method of treating one or more of such peripheral effects using a nitromethane derivative is also provided. In addition, the invention concerns novel nitromethane derivatives and processes for the manufacture of the said novel derivatives and for the preparation of medicaments containing any of the nitromethane derivatives.

The enzyme aldose reductase is responsible for the catalytic conversion of aldoses, such as glucose and galactose, to the corresponding alditols, such as sorbitol and galactitol respectively, in warm blooded animals such as man. Alditols penetrate cell membranes poorly and, once formed, tend to be removed only by further metabolism. Consequently, alditols tend to accumulate within cells where they are formed, causing a rise in internal osmotic pressure which may in turn be sufficient to destroy or impair the function of the cells themselves. In addition, raised alditol levels may result in abnormal levels of their metabolites which may themselves impair or damage cellular function. The enzyme aldose reductase has a relatively low affinity and is generally only effective in the presence of relatively large concentrations of aldose. Such large concentrations are present in the clinical conditions of diabetes (excessive glucose) and galactosemia (excessive galactose). Consequently, aldose reductase inhibitors are useful in the reduction or prevention of the development of those peripheral effects of diabetes or galactosemia which may be due in part to the accumulation of sorbitol or galactitol, respectively, in tissues such as the eye, nerve and kidney. Such peripheral effects include, for example, macular oedema, cataract, retinopathy, neuropathy and impaired neural conduction. Although a number of aldose reductase inhibitors have been discovered and clinically evaluated, there is a continuing need for alternative inhibitors. The present invention is based in part on this need and on our discovery of the unexpected inhibition of the enzyme aldose reductase by certain nitromethane derivatives.

According to the invention there is provided a novel pharmaceutical composition which comprises as active ingredient a nitromethane of the formula I of the structure $Q.SO_2.CH_2.NO_2$ wherein Q is an aromatic moiety of 6, 10 or 14 atoms optionally bearing 1, 2 or 3 substituents, independently selected from: hydrogen, halogeno, cyano, nitro, hydroxy, carboxy, amino, alkylamino or dialkylamino of up to 6 carbon atoms, (1–6C)alkanoylamino, (1–6C)alkanoyl, (1–6C)alkyl, (2 6C)alkenyl, (3 6C)alkenyloxy, fluoro(1–4C)alkyl, (1–6C)alkoxy, fluoro(1–4C)alkoxy, hydroxy(1–6C)-alkyl, (1–4C)alkoxy(1–4C)alkyl, carbamoyl, alkyl or dialkylcarbamoyl of up to 7 carbon atoms, sulphamoyl, alkyl or dialkylsulphamoyl of up to 6 carbon atoms, (1–6C)alkoxycarbonyl, (1–4C)alkylenedioxy, (1–6C)alkanesulphonamido, (1–6C)alkyl.S(O)$_n$— [in which n is zero, 1 or 2], phenyl, phenoxy, benzyloxy, benzyloxycarbonyl, benzamido and benzenesulphonamido, the benzene moiety of the last six groups optionally bearing a halogeno, (1–4C)alkyl or (1–4C)alkoxy substituent; or Q bears 4 or 5 substituents independently selected from halogeno, cyano, (1–6C)alkyl or (1–6C)alkoxy; but excluding the compounds in which Q is 2 carboxy- phenyl; or a non-toxic salt of said nitromethane of formula I; together with a pharmaceutically acceptable diluent or carrier.

In this specification the term "alkyl" includes both straight and branched alkyl groups but references to individual alkyl groups such as "propyl" are specific for the straight chain ("normal") version only, any branched chain isomer such as "isopropyl" being referred to specifically. An analogous convention applies to other generic terms.

It is to be understood that, insofar as certain of the compounds of formula I defined above may exist in optically active or racemic forms by virtue of one or more substituents containing an asymmetrically substituted atom, the invention includes in its definition of active ingredient any such optically active or racemic form which possesses the property of inhibiting the enzyme aldose reductase. The synthesis of optically active forms may be carried out by standard techniques of organic chemistry well known in the art, for example by synthesis from optically active starting materials or by resolution of a racemic form. Similarly, the inhibitory properties against aldose reductase may be evaluated using the standard laboratory tests referred to hereinafter.

A particular value for the aromatic moiety Q is a carbocyclic aromatic moiety, for example, phenyl, naphthyl, phenanthryl or anthryl, of which values phenyl and naphthyl are especially preferred.

Specific values for an optional substituent which may be present on Q include the following by way of example:

for halogeno: fluoro, chloro, bromo and iodo;
for alkylamino or dialkylamino of up to 6 carbon atoms; methylamino, ethylamino, propylamino, butylamino, dimethylamino, diethylamino and (methyl)(propyl)amino;
for (1–6C)alkanoylamino: (1–4C)alkanoylamino, such as formamido, acetamido and propionamido;
for benzamido optionally bearing a substituent: benzamido optionally bearing a fluoro, chloro, bromo, methyl, ethyl, methoxy or ethoxy substituent;
for (1–6C)alkanoyl: formyl and (2–4C)alkanoyl, such as acetyl, propionyl and butyryl;
for (1–6C)alkyl: (1–4C)alkyl, such as methyl, ethyl, propyl, isopropyl, butyl, sec-butyl and t butyl;
for (2 6C)alkenyl: (2 4C)alkenyl, such as vinyl, allyl, 1-propenyl and 2-methyl-2-propenyl;
for (3 6C)alkenyloxy: allyloxy, 2-methyl-2-propenyloxy and 3-methyl-3-butenyloxy;
for fluoro-(1–4C)alkyl: trifluoromethyl, pentafluoroethyl, 2,2,2-trifluoroethyl and 3,3,3-trifluoropropyl;
for (1–6C)alkoxy: (1–4C)alkoxy, such as methoxy, ethoxy, propoxy, isopropoxy, butoxy and t-butoxy;
for fluoro-(1–4C)alkoxy: trifluoromethoxy, 2,2,2-trifluoroethoxy and pentafluoroethoxy;
for phenyl, phenoxy, benzyloxy or benzyloxycarbonyl optionally bearing a substituent: phenyl, phenoxy, benzyloxy or benzyloxycarbonyl optionally bearing a fluoro, chloro, bromo, methyl, ethyl, methoxy or ethoxy substituent;
for hydroxy-(1–6C)alkyl: hydroxy-1–4C)alkyl, such as hydroxymethyl, 1-hydroxyethyl, 2-hydroxyethyl and 3 -hydroxypropyl;

for (1-4C)alkoxy(1-4C)alkyl: methoxymethyl, ethoxymethyl, 1-methoxyethyl, 2-methoxyethyl and 3-methoxypropyl;

for (1-6C)alkoxycarbonyl: (1-4C)alkoxycarbonyl, such as methoxycarbonyl, ethoxycarbonyl, isopropoxycarbonyl and t-butoxycarbonyl;

for (1-4C)alkylenedioxy: methylenedioxy, ethylenedioxy and isopropylidenedioxy, attached to adjacent atoms on the aromatic moiety Q; for (1-6C)alkanesulphonamido: (1 4C)alkanesulphonamido, such as methanesulphonamido, ethanesulphonamido and butanesulphonamido; for benzenesulphonamido optionally bearing a substituent: benzenesulphonamido optionally bearing a fluoro, chloro, bromo, methyl, ethyl, methoxy or ethoxy substituent;

for alkyl or dialkylcarbamoyl of up to 6 carbon atoms: N-methylcarbamoyl, N,N-dimethylcarbamoyl, N-ethylcarbamoyl, N,N-diethylcarbamoyl and N,N dipropylcarbamoyl;

for alkyl or dialkylsulphamoyl of up to 6 carbon atoms: N-methylsulphamoyl, N-ethylsulphamoyl, N-propylsulphamoyl, N-butylsulphamoyl, N,N-dimethylsulphamoyl and N,N-dipropylsulphamoyl; and for (1-6C)alkyl.S(O)$_n$—: (1-4C)alkyl.S(O)$_n$— such as methylthio, ethylthio, methylsulphinyl, ethylsulphinyl, methylsulphonyl and ethylsulphonyl.

In general Q is typically phenyl or naphthyl optionally bearing up to 3 substituents.

Certain of the nitromethane derivatives are already known. For example, the derivatives of formula I wherein Q is phenyl or 4-methylphenyl are described as chemical intermediates in U.S. Pat. No. 4,053,633 during the preparation of the corresponding dibromonitromethane derivatives which are anti-microbial agents. Similarly, the derivatives of formula I wherein Q is phenyl or 4 fluoro-, 4 chloro-, 4-methyl- or 4-acetamido-phenyl are described without any utility by Kelley et al in J. Heterocyclic Chemistry, 1977, 14, 1415-1416. Similarly, the derivatives of formula I wherein Q is 4-vinylphenyl, 2-carboxyphenyl and 4-bromophenyl are described as chemical intermediates in J. Polymer Science, Polymer, Chem. Ed., 1985, 23(7), 1963-72, Chemical Abstracts, Vol.59, Abstract No. 6341 g, and J. Pract. Chem., 1920, 101, 136-157, respectively. However, prior to the present invention, it was not known that any of these nitromethane derivatives possessed the property of inhibiting the enzyme aldose reductase.

A particular group of known nitromethane derivatives useful as aldose reductase inhibitors comprises compounds of the formula II of structure X.Q.SO$_2$.CH$_2$.NO$_2$ in which Q is benzene and X is hydrogen or a methyl, fluoro, chloro, bromo or acetamido substituent attached at the 4-position of Q and non-toxic salts thereof. The invention further includes pharmaceutical compositions comprising as active ingredient such a compound of the formula II or a non-toxic salt thereof, together with a pharmaceutically acceptable diluent or carrier. Also included in the invention is a method of treating or preventing one or more of the peripheral effects of diabetes or galactosemia by administration of an effective amount of a compound of the formula I or II or of a non-toxic salt thereof. A further feature of the invention is the use of a compound of the formula I or II as defined above or of a non-toxic salt thereof in the manufacture of a novel medicament for use in the treatment or prevention of one or more of the peripheral side-effects of diabetes or galactosemia.

Particular known compounds of formula II which are of special interest as aldose reductase inhibitors for use in the invention include, for example: (phenylsulphonyl)nitromethane, (4-bromophenylsulphonyl)nitromethane and (4-methylphenylsulphonyl) nitromethane, and the non-toxic salts thereof.

The compositions of the invention may be in various conventional forms. Thus, they may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions) or for parenteral administration (for example as a sterile aqueous or oily solution for intravenous, subcutaneous, intramuscular or intravascular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or alginic acid; binding agents such as gelatin or starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as arachis oil, liquid paraffin or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharin or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents, such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, or esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedures well known in the art. Topical formulations for administration to the eye will generally be in the form of an ointment, gel or sterile solution buffered at an opthalmically acceptable pH, for example in the range pH 7.0-7.6.

The amount of active ingredient that is combined with one or more excipients to produce a single dosage form will necessarily vary depending upon the host treated and the particular route of administration. For example, a formulation intended for oral administration to humans will generally contain for example from 0.5 mg to 2 g of active agent compounded with an appropriate and convenient amount of excipients which may vary from about 5 to about 98% by weight of the total composition. Dosage unit forms will generally contain about 1 mg to about 500 mg of an active ingredient.

Suitable non-toxic salts include, for example, pharmaceutically acceptable salts such as alkali metal (such as potassium or sodium), alkaline earth metal (such as calcium or magnesium), ammonium and aluminium salts, and salts with organic bases affording physiologically acceptable cations, such as salts with methylamine, dimethylamine, trimethylamine, piperidine and morpholine. In addition, for those active ingredients which are sufficiently basic (for example those which contain an alkylamino or dialkylamino group), suitable non-toxic salts include, for example, pharmaceutically and physiologically acceptable acid-addition salts such as salts with hydrogen halides, sulphuric acid, phosphoric acid, citric acid and maleic acid.

The majority of the nitromethane derivatives of formula I are novel. According to a further feature of the invention there is provided a novel compound of the formula I, or a non-toxic salt thereof, as defined hereinbefore for active ingredients in the compositions of the invention, but excluding those compounds wherein Q is unsubstituted phenyl and phenyl bearing a 4-fluoro, 4-chloro, 4-bromo, 4-methyl, 4-vinyl, 4-acetamido or 2-carboxy substituent, and the alkali metal salts thereof.

Specific values for Q and for the optional substituents thereon in the above definition include any of those defined hereinbefore, subject to the above exclusion.

One group of novel compounds of the invention of particular interest comprises compounds of the formula III (set out hereinafter) wherein $X^1$ is selected from halogeno, (1-6C)alkyl, (1-6C)alkoxy, (3-6C)alkenyloxy, hydroxy, cyano, hydroxy-(1-6C)alkyl, fluoro-(1-4C)alkyl; $X^2$ is hydrogen or one of the values of $X^1$; and $X^3$ is hydrogen or one of the substituents on Q defined above in the definition of active ingredients of the invention, provided that $X^2$ and $X^3$ are not both hydrogen when $X^1$ is 4-fluoro, 4-chloro, 4-bromo, 4-methyl or 2-carboxy; together with the non-toxic salts thereof.

Still further groups of novel compounds of the invention comprise those compounds of the formula I wherein Q is:
a) naphthyl;
b) phenanthryl; or
c) anthryl;
and, in each group, Q is unsubstituted or bears up to 3 substituents selected from any of those defined for $X^1$, $X^2$ and $X^3$ hereinabove; together with the non-toxic salts thereof.

Preferred values for $X^1$ include, for example, halogeno and (1-6C)alkyl (and especially, fluoro, chloro and methyl). Preferred values for $X^2$ include, for example, hydrogen and (1-6C)alkyl (and especially, hydrogen and methyl). Preferred values for $X^3$ include, for example, hydrogen, halogeno and (1-6C)alkyl (and especially, hydrogen, fluoro, chloro, and methyl).

Novel compounds of the invention are described in the accompanying Examples and, of these, compounds of particular interest include Examples 1, 2, 6, 7, 9, 19, 20, 30, 46, 50, 62, 63, 65, 66, 71 and 73, which are provided, together with their non-toxic salts, as a further feature of the invention.

The novel compounds of the invention may be obtained by standard procedures of organic chemistry already known for the production of structurally analogous compounds, for example by one or more of the procedures reviewed in the paper by Zeilstra et alia in Rec.Trav.Chim.Pays Bas 1974, 93, 11 14. Such procedures are provided as a further feature of the invention and are illustrated by the following procedures in which Q and the optional substituents thereon have any of the meanings defined hereinbefore.

a) Reacting an alkali metal sulphinate (IV) of the formula $Q.SO_2^-M^+$ wherein $M^+$ is an alkali metal cation, such as sodium or potassium, with nitromethane and iodine in the presence of an alkali metal (1–6C)alkoxide such as potassium t-butoxide or sodium methoxide.

The reaction is preferably carried out in the presence of a suitable polar solvent, for example, dimethylformamide (which is preferred) or N-methyl-2 pyrrolidone, and at a temperature in the range, for example, $-30°$ to $20°$ C. and, conveniently, at about $0°$ C. The nitromethane is generally present in an excess.

The alkali metal sulphinates may be obtained from the corresponding sulphinic acids of the formula $Q.SO_2H$ by reaction with the appropriate alkali metal hydroxide or (1–6C)alkoxide such as sodium or potassium methoxide or ethoxide. The sulphinic acids may themselves be obtained from the corresponding sulphonyl chlorides of the formula $Q.SO_2Cl$ by a conventional reduction using sodium sulphite or zinc dust and water. The sulphonyl chlorides may in general be obtained by sulphonation of the appropriate compound of the formula Q.H to give the sulphonic acid of the formula $Q.SO_3H$, which is then converted to the sulphonyl chloride, for example, by reaction with phosphorus pentachloride. (b) Reacting a sulphone (V) of the formula $Q.SO_2.CH_3$ with a (1–5C)alkyl nitrate, such as ethyl, propyl, isopropyl or amyl nitrate in the presence of a strong base.

A particularly suitable strong base is, for example, an alkali metal (1–6C)alkane such as butyllithium.

The reaction is preferably carried out in the presence of a suitable solvent or diluent, for example an ether such as tetrahydrofuran or t-butyl methyl ether, and at a temperature in the range, for example, $-80°$ to $10°$ C.

The necessary sulphones of the formula V may be made by standard procedures well known in the art, for example by oxidation of the corresponding methylthio compound (VI) of the formula $Q.S.CH_3$ using analogous conditions to those described for process (c) below. (c) Oxidising a thioether (VII) of the formula $Q.S.CH_2.NO_2$.

Suitable oxidising agents include those which are well known in the art for the conversion of thio to sulphonyl groups and which are compatible with the presence of other sensitive functional groups which may be present as substituents on Q. Thus, for example, hydrogen peroxide, an organic peracid (such as perbenzoic acid) or lead tetraacetate may be used. Alternatively, an alkali metal periodate (such as sodium metaperiodate), persulphate (such as potassium monopersulphate) or permanganate (such as potassium permanganate), or gaseous oxygen in the presence of a suitable catalyst such as platinum, may be employed. The oxidation is preferably carried out in a suitable conventional solvent or diluent for such oxidations, for example in acetic or propionic acid, and at a temperature in the general range, for example $0°$ to $80°$ C.

In certain cases, the corresponding sulphoxide derivative of the thioether of formula VII may be formed as an isolable intermediate. The process of the invention also includes the oxidation of such a sulphoxide intermediate to a sulphone of formula I, for example, by reaction with an alkali metal permanganate (such as potassium permanganate) in a suitable solvent such as acetic acid and at a temperature in the range, for example, $20°$ to $80°$ C.

The starting thioethers of formula VII may be obtained by conventional procedures of organic chemistry, for example, from a potassium or sodium salt of the corresponding thiophenol (VIII) of the formula Q.SH by conversion to the corresponding thioacetic acid (IX) of the formula $Q.S.CH_2CO_2H$ (or a (1–4C)alkyl ester thereof, such as a methyl or ethyl ester) by reaction with chloro- or bromo-acetic acid (or a (1–4C)alkyl ester thereof) in the presence of a suitable base. The acid IX (or a (1–4C)alkyl ester thereof) is then reacted with a (1–5C)alkyl nitrate and an alkali metal (1–6C)alkane, for example propyl nitrate and butyllithium, under similar conditions to those used for process (b) above, to give the alkali metal salt of the corresponding 2 nitroacetic acid (XI) of the formula $Q.S.CH(NO_2).CO_2H$ (or of the (1–4C)alkyl ester thereof). The acids of formula XI are unstable and readily decarboxylate and acidification of the alkali metal salt of an acid of formula XI allows the isolation of a thioether of formula VII. An ester of an acid of formula XI may be hydrolysed, for example, using aqueous base, to the acid of formula XI and then acidified to produce a thioether of formula VII. The esters of the acids of formula XI may also conveniently be obtained by reacting the appropriate (1–4C)alkyl nitroacetate with the required sulphenyl chloride (formula VIII, H replaced by chloro) in the presence of a base such as potassium fluoride.

It will be appreciated that in the formula I compounds of the invention Q may bear a wide variety of reactive substituents. Accordingly, it may be necessary to protect one or more such reactive substituents in a conventional manner with an appropriate protecting group at some stage prior to carrying out one of the above procedures (a)–(c) and then to remove the protecting group as a final step. Thus, for example, a hydroxy substituent may be protected using, for example, an acyl (such as acetyl or benzoyl), t-butyl, allyl or benzyl protecting group; an amino substituent may be protected using, for example, an acyl (such as acetyl or benzoyl) protecting group; a ketone group may be protected as its ketal (for example as its ketal with 1,2-ethanediol); and a carboxy substituent may be protected, for example, in the form of its (1–4C)alkyl (especially methyl, ethyl or t-butyl) or benzyl ester. The appropriate protecting groups and the procedures necessary for the protection and deprotection of reactive substituents is well described in standard text-books of organic chemistry. The invention includes a development of one of the processes (a), (b) or (c) for the production of a novel compound of formula I, as defined hereinbefore, which is characterised by using a starting material of the formula IV, V or VII respectively in which one or more of any reactive substituents present as substituents on Q (such as hydroxy, amino, ketone or carboxy groups) have been protected with appropriate protecting groups and carrying out the appropriate removal of the protecting group as a final step.

In addition, it will be appreciated that many of the substituents on Q may be obtained from other substituents in compounds of the formula I, themselves first obtained by process (a), (b) or (c) above, using standard functional group interconversions well known in the art. Such interconversions include, for example:

(1) reaction of an amino group with an acylating agent such as an alkanoic acid chloride, mixed alkanoic acid anhydride, or an alkyl or benzyl chloroformate, in the presence of a base such as triethylamine at about ambient temperature;

(2) hydrolysis of an alkanoylamino group by reaction with a strong acid or base in a suitable solvent such as a (1-4C)alkanol at a temperature in the range 35° to 80° C.;

(3) condensation of a carboxy group (or the corresponding carbonyl chloride or bromide) with the appropriate alkanol, benzyl alcohol or amine, in the presence of a suitable condensing agent (that is, generally, in the presence of a carbodiimide when a free carboxy group is used and in the presence of a base such as triethylamine when the carbonyl chloride or bromide is used) at about ambient temperature;

(4) reaction of a bromo or iodo group with a lithiating agent such as butyllithium, followed by reaction with carbon dioxide, at a temperature of $-70°$ to $0°$ C.;

(5) reduction of a formamido group to a methylamino group using a suitable reducing agent (such as borane, conveniently as a complex with methyl sulphide) at a temperature in the general range $0°$ to $25°$ C.;

(6) reduction of a carboxy group to a hydroxymethyl group using a suitable reducing reagent (such as borane, conveniently as a complex with methyl sulphide) at a temperature in the range $10°$ to $40°$ C.;

(7) dehydration of a carbamoyl group to a cyano group using a suitable dehydrating agent (such as phosphoryl chloride) at a temperature in the range $60°-110°$ C.;

(8) oxidising an alkylthio to an alkylsulphinyl and/or alkylsulphonyl group, and an alkylsulphinyl to an alkylsulphonyl group, using an appropriate oxidising agent (such as potassium monopersulphate for converting an alkylthio to an alkylsulphinyl group, or potassium permanganate for converting an alkylthio or an alkylsulphinyl to an alkylsulphonyl group), using similar conditions to those specified for process (c) above;

(9) oxidising an hydroxyalkyl group to the corresponding keto group using a suitable oxidising agent (such as pyridinium chlorochromate) at about ambient temperature; and

(10) reductively alkylating an amino group to the corresponding alkylamino or dialkylamino group by reaction with the appropriate alkanoic acid and sodium borohydride at a temperature in the range $20°$ to $80°$ C.

The majority of such interconversions are illustrated in the accompanying Examples and are included as a further feature of the invention.

Whereafter, when a non-toxic salt is required, a compound of formula I may be reacted with an appropriate base having a non-toxic cation, and, when Q contains a suitably basic group (such as alkylamino or dialkylamino), a non-toxic, acid-addition salt may be prepared by reaction with an appropriate acid having a non-toxic anion.

As stated previously, the compounds of formula I inhibit the enzyme aldose reductase. The compounds are thus of value, for example, in treating those diseases or conditions which are caused by excessive quantities of the products such as sorbitol formed in the body by processes catalysed by the enzyme aldose reductase.

The property of inhibiting the enzyme aldose reductase in vivo may be demonstrated in the following standard laboratory test. Thus, rats are made diabetic (as evidenced by severe glucosuria being present) by dosing with streptozotocin. The animals are then dosed daily with the test compound for one, two or five days. The animals are then killed 2–6 hours after the final dose and the eye lenses and/or sciatic nerves are removed. After a standard work-up procedure, the residual sorbitol levels in each tissue are determined by gas liquid chromatography after conversion to the poly-trimethylsilyl derivatives. Inhibition of aldose reductase in vivo is then assessed by comparing the residual sorbitol levels in tissues from the dosed diabetic group of rats with those of an undosed group of diabetic rats and an undosed, normal group of rats.

The property of inhibiting the enzyme aldose reductase may also be demonstrated in vitro. Thus, partially purified aldose reductase is isolated in known manner from bovine lenses. The percentage inhibition of this enzyme's ability in vitro to catalyse the reduction of aldoses to polyhydric alcohols, and particularly to reduce glucose to sorbitol, caused by a test compound is then determined using standard spectrophotometric methods.

By way of illustration of the aldose reductase inhibitory properties of compounds of formula I, the compound of Example 1 had an $IC_{50}$ of $3.2 \times 10^{-7}$M in the above in vitro test. Although the activity of individual compounds of formula necessarily varies to some extent with chemical structure, in general, compounds of the formula I show significant inhibition in the above mentioned in vivo test at a dose (generally p.o.) of 100 mg/kg or much less with no evidence of overt toxicity, and have an $IC_{50}$ in the above mentioned in vitro test of $10^{-5}$M or much less.

The compounds of formula I will primarily be administered systemically (generally by mouth) to a warmblooded animal to produce a therapeutic or prophylactic effect mediated by inhibition of the enzyme aldose reductase, for example at a daily dose in the range of 1 to 40 mg/kg. In man, it is envisaged that a total daily dose in the range 15 to 800 mg per man will be administered, given if necessary, in divided doses.

However, the precise amount of compound administered will naturally vary somewhat, for example, the age and sex of the patient and the severity and extent of the condition being treated.

The compounds of formula I may also be administered topically, for example by topical administration direct to the tissue or organ in which inhibition of the enzyme is required, for example by topical administration to the eye. The precise amount of compound administered will necessarily depend on the formulation used. Thus, for example, when a solution is administered, a concentration of the compound containing up to 0.01% by weight will generally be used. Similarly, when an ointment is administered, a concentration of the compound of up to 2% by weight will generally be used. Topical formulations of compounds of formula I may be administered to the eye of an animal, for example, man or dog, requiring treatment and/or prevention of diabetic cataracts or retinopathy, in a conventional manner, for example, using a drop or eyewash topical formulation.

The compositions may also contain one or more other agents which are known to have a useful effect in the treatment of diabetes or galactosemia, for example a hypoglycaemic agent such as tolbutamide, chlorpropamide or glybenclamide.

The invention will now be illustrated by the following non-limiting Examples in which, unless otherwise stated:

(i) all evaporations were carried out by rotary evaporation in vacuo.

(ii) all operations were carried out at room temperature, that is in the range 18°-26° C.:

(iii) the purity of chemical products was assessed by nuclear magnetic resonance spectroscopy, thin layer chromatographic analysis and/or microanalysis; (iv) "mmol" stands for millimolecular equivalents;

(v) petroleum ether (b.p. 60°-80° C.) is referred to as petrol 60°-80°;

(vi) yields are for illustration only and are not necessarily the maximum attainable by diligent process development; and (vii) medium pressure liquid chromatography (MPLC) was carried out on silica (Merck Art. 9385, available from E Merck and Co., Darmstadt, West Germany).

EXAMPLE 1

To a solution of potassium t-butoxide (6.27 g, 55.8 mmol) in N,N-dimethylformamide (DMF: 250 ml), cooled to 0° C. in an ice-bath, was added nitromethane (6.72 ml, 124 mmols) dropwise with stirring. When the addition was complete, stirring was continued for an additional 30 minutes at 0° C. Naphthalene-1-sulphinic acid sodium salt (12 g, 56 mmol) was then added, followed immediately by iodine (7.2 g, 28.3 mmol). The mixture was stirred overnight and allowed to attain room temperature. A concentrated solution of aqueous sodium sulphite was added to partially decolourise the reaction mixture, which latter was then poured into water (1 liter) and acidified with 2M hydrochloric acid. The aqueous mixture was extracted with ethyl acetate. The extracts were combined, washed with water, brine, and dried (MgSO$_4$). The solvent was removed by evaporation and the residual yellow liquid was purified by medium pressure liquid chromatography (MPLC) on silica, eluting with ethyl acetate-hexane (1:10 v/v, gradually increasing to 1:5 v/v). There was thus obtained (1-naphthylsulphonyl)nitromethane as a colourless oil which crystallised from ether to give a solid (1.85 g), m.p. 99°-101° C.

The starting material was obtained as follows:

To a vigorously stirred solution of sodium bicarbonate (8.4 g, 100 mmol) and anhydrous sodium sulphite (12 g, 95 mmol) in water (50 ml) at 70°-80° C., was added naphthalene-1-sulphonyl chloride (11.5 g, 50 mmol) in portions and with vigorous stirring. The temperature was kept at 70°-80° C. by intermittent heating. When the addition was complete, the mixture was heated and stirred at 70°-80° C. for a further hour. The mixture was then allowed to cool to room temperature over 4 hours and acidified with 2M hydrochloric acid. The precipitated solid was collected by filtration, washed with water, air dried and then recrystallised from aqueous ethanol to give naphthalene-1-sulphinic acid as a solid (6.0 g), m.p. 86 87° C.

This acid was converted to its sodium salt by addition to a solution of sodium methoxide (1 equivalent) in methanol and evaporation of the resultant solution. This sodium salt was used without purification or characterisation.

EXAMPLE 2

Using a similar procedure to that described in Example 1, there was obtained (2,4,6-trimethylphenylsulphonyl)nitromethane as a solid, m.p. 92°-93° C. (recrystallised from ethyl acetate/hexane). The starting sulphinic acid sodium salt was obtained in an analogous manner to that for the starting material in Example 1 using 2,4,6-trimethylbenzenesulphonyl chloride as the initial reagent.

EXAMPLE 3

Nitromethane (12.0 g, 100 mmol) was added dropwise to a stirred solution of potassium t-butoxide (20 g, 178 mmol) in dry DMF (200 ml), the temperature being controlled at 0°-5° C. by external cooling. After addition was complete the mixture was stirred for an additional 30 minutes at 0°-5° C. Sodium 4-iodobenzenesulphinate (29.0 g, 100 mmol) was then added, followed by iodine (22.8 g, 90 mmol). The mixture was stirred at ambient temperature for 2 hours and then poured into water (3 liters). A concentrated solution of aqueous sodium sulphite was added to partially decolourise the reaction mixture, which was then acidified with 2M hydrochloric acid. The precipitated solid was collected by filtration, washed with water and then recrystallised 4 times from ethanol to give (4-iodophenylsulphonyl)nitromethane as a crystalline solid (0.8 g), m.p. 177°-179° C., microanalysis, found C, 25.56; H, 1.83; N, 4.18% C$_7$H$_6$INO$_4$S requires: C, 25.70; H, 1.85; N 4.30%.

The starting sulphinate salt was obtained as follows:

4-Iodobenzenesulphonyl chloride (30.2 g, 100 mmol) was added in portions to a vigorously stirred solution of sodium bicarbonate (16.8 g, 200 mmol) and anhydrous sodium sulphite (24 g, 190 mmol) in water (100 ml) at 70°-80° C. The temperature was kept at 70°-80° C. by intermittent heating. When the addition was complete, the mixture was heated and stirred at 70°-80° C. for a further hour. The mixture was then filtered and the filtrate allowed to cool to approximately 40° C. The resulting solid which crystallised from the solution was separated by filtration, washed with ice-cold water and dried in vacuo for 48 hours over sodium hydroxide and calcium chloride, to give sodium 4-iodobenzenesulphinate m.p. >350° C., which was used without further purification or characterisation.

EXAMPLES 1-12

Using a similar procedure to that described for (4-iodophenylsulphonyl)nitromethane in Example 3, the following compounds of formula I were obtained in yields of 1-30% and had satisfactory elemental analyses and NMR spectra:

| Example | Q | m.p. (°C.) | recrystallisation solvent(s) |
|---|---|---|---|
| 4 | 3,5-di(trifluoromethyl)phenyl | 76-78 | hexane |
| 5 | 4-trifluoromethoxyphenyl | 110-112 | toluene/hexane |
| 6 | 3-chlorophenyl | 67-69 | toluene/hexane |
| 7 | 3,4-dichlorophenyl | 92-94 | methanol |
| 8 | 3-methylphenyl | 67-69 | ethanol |
| 9* | 2-methylphenyl | 47-49 | toluene/hexane |
| 10 | 4-hexylphenyl | 95-97 | ethanol |
| 11 | 4-butoxyphenyl | 84-86 | methanol |
| 12* | 4-benzyloxyphenyl | 115-117 | ethyl acetate |

[*This compound was obtained from the acidified reaction mixture by extraction with dichloromethane. The extracts were dried (Na$_2$SO$_4$) and the solvent evaporated. The residue was then purified by flash chromatography using 7:3 v/v hexane/ethyl acetate as eluant.]

The necessary sodium sulphinate salts of formula IV were in general made using an analogous procedure to that described for sodium 4-iodobenzenesulphinate in Example 3 and were obtained as solids of high melting point which were used without full characterisation. However, in the case of the sulphinate starting materials for Examples 8 and 9, the sulphite reaction mixture was diluted with water, acidified to pH 1 with concentrated hydrochloric acid and then extracted with dichloromethane. The extracts were dried ($Na_2SO_4$) and the solvent evaporated. The resultant sulphinic acid was then converted to its sodium salt by treatment with an equivalent amount of methanolic sodium methoxide and subsequent evaporation of the methanol.

The required starting sulphonyl chlorides were either commercially available or made by standard methods well known in the art, for example by chlorosulphonation of the appropriate compound of the formula Q-H using a procedure based on that described in Organic Syntheses, Collected Volume 1, at page 85, or by reaction of the appropriate diazonium salt with sulphur dioxide using a procedure based on that described in Organic Syntheses, Volume 60, at page 121. The sulphonyl chlorides for Examples 11 and 12 were obtained using the procedure described in Helvetica Chimica Acta, 1956, 39, 1579–1586.

EXAMPLE 13

A solution of potassium peroxymonosulphate ['Oxone' (trade mark); 38.7 g, 63 mmol] in water (100 ml) was added in one portion to a vigorously stirred solution of (4-t-butylphenylthio)nitromethane (A) (4.76 g, 21.9 mmol) in methanol (90 ml). A cream coloured precipitate was formed. The mixture was stirred overnight. Water (200 ml) was then added and the mixture was extracted with ethyl acetate. The extracts were combined, dried ($MgSO_4$) and the solvent was removed by evaporation. The residual yellow solid was recrystallised from cyclohexane to give (4 t-butylphenylsulphonyl)nitromethane, as a colourless solid (3.34 g), m.p. 90°–91° C., microanalysis found: C, 51.4; H, 5.9; N, 5.4%; $C_{11}H_{15}NO_4S$: requires: C, 51.4; H, 5.9; N, 5.4%.

The starting material (A) was obtained as follows:

(i) Sodium chloroacetate (6.29 g, 54 mmol) was added in portions to a solution of 4-t-butylbenzenethiol (9.0 g, 54 mmol) in a 30% (w/v) aqueous solution of sodium hydroxide (10.8 ml, 81 mmol) with stirring at 80° C. When the addition was complete, stirring was continued for an additional 2 hours at 80° C., during which time a thick white precipitate had formed. The reaction mixture was added to water (200 ml) and was acidified to pH 2 by the addition of 2M hydrochloric acid. The mixture was extracted with ethyl acetate. The combined extracts were then extracted with a 10% (w/v) aqueous solution of potassium carbonate. The aqueous extracts were acidified to pH 2 by the addition of 2M hydrochloric acid and again extracted with ethyl acetate. These combined extracts were dried ($MgSO_4$) and the solvent was removed by evaporation to give 2-(4-t-butylphenylthio)acetic acid (B) as a straw coloured oil (9.07 g); which had a satisfactory NMR spectrum.

(ii) A 1.6 M solution of butyllithium in hexane (51.25 ml, 82 mmol) was added dropwise to a stirred solution of B (9.07 g, 40.5 mmol) in anhydrous tetrahydrofuran (150 ml) maintained a −40° C. under an atmosphere of argon. When the addition was complete, the mixture was stirred for 1 hour at −5° C. Propyl nitrate (12.92 g, 123 mmol) was added dropwise to the stirred mixture at −5° C., which was then stirred for a further 2 hours, maintaining the temperature below 0° C. throughout. The mixture [containing the dilithium salt of 2-(4-t-butylphenylthio) 2-nitroacetic acid] was acidified to pH 2 by addition of 2M hydrochloric acid. The mixture was allowed to stand for 30 minutes at ambient temperature after which time evolution of carbon dioxide [obtained from decarboxylation of 2-(4-t-butylphenylthio) 2-nitroacetic acid] had ceased. Water (300 ml) was then added and the mixture was extracted with ethyl acetate. The combined extracts were washed successively with an aqueous solution of sodium hydrogen carbonate, water and brine, and then dried ($MgSO_4$) and the solvent removed by evaporation. The residual oil was purified by chromatography on silica, eluting with (3:20 v/v) ethyl acetate/hexane, to give (4-t-butylphenylthio)nitromethane (A) as an orange oil (4.76 g), NMR spectrum (200 MHz, $d_6DMSO$): 1.27 (s, 9H), 6.02 (s, 2H), 7.42 (s, 4H).

EXAMPLES 14–16

Using a similar procedure to that described in Example 13, but starting from the appropriate thioether of formula VII, the following compounds were obtained:

(Example 14): (3-methoxyphenylsulphonyl)nitromethane, as a solid, m.p. 57°–58° C.; [purified by MPLC using ethyl acetate/hexane (1:10 v/v)]; microanalyis, found: C, 42.1; H, 4.0; 5.95; $C_8H_9NO_5S$ requires: C, 41.6; H, 3.9; N, 6.1%, in 77% yield, starting from (3-methoxyphenylthio)nitromethane [itself isolated as an oil having a satisfactory NMR spectrum (90 MHz, $CDCl_3$): 3.79 (s, 3H), 5.41 (s, 2H), 6.74–7.34 (m, 4 aromatic H), after purification by MPLC using ethyl acetate/hexane (1:5 v/v)];

(Example 15): (3-trifluoromethylphenylsulphonyl)nitromethane, as a solid m.p. 96°–97° C.; microanalysis, found: C, 36.1; H, 2.3; N, 4.9%; $C_8H_6F_3NO_4S$ requires: C, 35.7%; H, 2.2; N, 5.2%; (purified by sublimation); in 42% yield, starting from (3-trifluoromethylphenylthio)nitromethane [itself isolated as an oil having a satisfactory NMR spectrum (200 MHz, $CDCl_3$): 5.49 (s, 2H) 7.45–7.83 (m, 4 aromatic H), after purification by MPLC using ethyl acetate/hexane (7:3 v/v)]; and (Example 16): (2-naphthylsulphonyl)nitromethane, as a solid, m.p. 106°–107° C.; microanalysis, found: C, 52.9; H, 3.5; N, 5.5%; $C_{11}H_9NSO_4$ requires: C, 52.6; H, 3.6; N, 5.6%; [purified by MPLC using ethyl acetate/hexane (1:10 v/v)]; in 14% yield, starting from (2-naphthylthio)nitromethane [itself isolated as an oil after purification by MPLC using ethyl acetate/hexane (1:5 v/v)].

The starting thioethers of formula VII were obtained by analogy with that for Example 13, that is by nitration of a thioacetic acid of formula IX and subsequent acid-catalysed decarboxylation of the nitroacetic acid of formula XI. The thioacetic acids of formula IX were themselves obtained using an analogous procedure to that described for Example 13, that is by reaction of the appropriate thiol of formula VIII with sodium chloroacetate and sodium hydroxide. In general, the starting materials were not characterised.

EXAMPLE 17

A solution of potassium permanganate (1.68 g, 10.6 mmol) in water (56 ml) was added in one portion to a solution of (2,4,5-trichlorophenylthio)nitromethane (2.45 g, 9 mmol) in acetic acid (50 ml) at 20° C., and the mixture immediately cooled in an ice-bath. The mixture was stirred for ten minutes, diluted with water (100 ml), decolourised with sodium sulphite solution, and extracted with ethyl acetate (2×75 ml). The extracts were combined, dried (MgSO₄), and evaporated. The residue was triturated with hexane and the resultant solid removed by filtration. This was purified by MPLC, eluting with ethyl acetate/hexane (1:5 v/v). There was thus obtained (2,4,5-trichlorophenylsulphonyl)nitromethane as a colourless solid (0.8 g) m.p. 122°–123° C.; microanalysis, found: C 28.0; H 1.4; N 4.9%; C₇H₄Cl₃NO₄S requires: C 27.6; H 1.3; N 4.6%.

The starting thioether was itself obtained as an oil, NMR (200 MHz, CDCl₃)): 7.63 (s, 1H), 7.53 (s, 1H), 5.43 (s, 2H) [after purification by MPLC using ethyl acetate/hexane (1:5 v/v)], starting from 2,4,5-trichlorophenylthioacetic acid, itself obtained as a solid, m.p. 111°–112° C. (recrystallised from ethyl acetate/hexane) starting from 2,4,5-trichlorobenzenethiol, using analogous procedures to those described for Example 13.

EXAMPLES 18-19

Using a similar procedure to that described in Example 17 except that the oxidation was carried out at 50° C. for 3 hours, the following were obtained:

(Example 18): [4-(4-chlorophenyl)phenylsulphonyl]nitromethane, as a solid, m.p. 175 176° C. (after trituration with hexane), in 84% yield, starting from [4 (4-chlorophenyl)phenylthio]nitromethane [itself obtained as a solid having a satisfactory microanalysis and NMR spectrum (200 MHz/CDCl₃): 5.49 (d, 2H), 7.38–7.63 (m, 8H) after purification by MPLC using dichloromethane/hexane (7:3 v/v]; and (Example 19): (2,6-dimethylphenylsulphonyl)nitromethane, as a solid, m.p. 70°–71° C. [after purification by MPLC using ethyl acetate/hexane (1:10 v/v)]in 44% yield, starting from (2,6-dimethylphenylthio)nitromethane [itself obtained as an oil having a satisfactory NMR spectrum (200 MHz, CDCl₃): 2.52 (s, 6H), 5.25 (s, 2H), 7.10–7.26 (m, 3H) after purification by MPLC using ethyl acetate/hexane (1:5 v/v)].

The necessary thioethers of formula VII were obtained from the corresponding thioacetic acids of formula IX and thiols of formula VIII, by analogy with the procedures in Example 13. The thioacetic acids of formula IX were isolated as solids having satisfactory NMR spectra and were not otherwise characterised.

EXAMPLE 20

A freshly prepared solution of potassium permanganate in water (58.67 ml of a 3% w/v solution, 11.14 mmol) was added in one portion to a stirred solution of (4-chloro-2,5-dimethylphenylsulphinyl)nitromethane (2.0 g, 9.28 mmol) in acetic acid (75 ml). The mixture was stirred at 50° C. for 3 hours and then allowed to cool to ambient temperature. A saturated solution of sodium sulphite was added dropwise to partially decolourise the reaction mixture which was then poured into water (350 ml) and extracted three times with ether. The combined extracts were washed with brine and dried (MgSO₄). The solvent was removed by evaporation to give an oil (2.0 g). This was purified by MPLC eluting with dichloromethane to give (4-chloro-2,5-dimethylphenylsulphonyl)nitromethane as a solid (1.47 g, 60% yield), m.p. 113°–114° C. (after trituration of the solid with hexane); microanalysis, found: C, 41.1; H, 3.8; N, 5.2%; C₉H₁₀ClNO₄S requires: C, 41.0; H, 3.8; N, 5.3%.

The starting material was obtained as follows:

A solution of potassium peroxymonosulphate ('Oxone' trade mark, 29.7 g, 48.3 mmol) in water (70 ml) was added in one portion to a vigorously stirred solution of (4-chloro-2,5-dimethylphenylthio)nitromethane (A) (3.7 g, 18.5 mmol) in methanol (60 ml). An exothermic reaction occurred which was moderated by having the reaction vessel in a bath of water at ambient temperature. The mixture was stirred for 16 hours and then diluted with water (500 ml). The aqueous mixture was then extracted with ethyl acetate. The combined extracts were washed with water (until the washings were neutral), then with brine and dried (MgSO₄). Evaporation of the solvent gave (4-chloro-b 2,5-dimethylphenylsulphinyl)nitromethane as a pale yellow solid (2.95 g, 64% yield), m.p. 124°–125° C. (after recrystallisation from hexane/ethyl acetate); microanalysis, found: C, 43.6; H, 4.1; N, 5.5%; C₉H₁₀ClNO₃S requires: C, 43.6; H, 4.1; N, 5.7%.

The thioether (A) was obtained as an oil having a satisfactory NMR spectrum (200 MHz/CDCl₃): 2.33 (s, 3H), 2.42 (s, 3H), 5.37 (s, 2H), 7.26 (s, 1H), 7.35 (s, 1H) from (4-chloro-2,5-dimethylphenylthio)aceti acid, itself obtained from 4-chloro-2,5-dimethylbenzenethiol, in both cases using analogous procedures to those described in Example 13.

EXAMPLE 21

4-Fluoro-3,5-dimethylbenzenesulphonyl chloride (5.56 g, 25 mmol) was added in portions to a solution of anhydrous sodium sulphite (6.0 g, 47.6 mmol) and sodium bicarbonate (4.2 g, 50 mmol) in water (25 ml) at 70° C. with vigorous stirring. When the addition was complete, the mixture was heated and stirred at 70° C. for a further 2 hours. The mixture was allowed to cool. The solid which crystallised from the solution was collected by filtration, dissolved in the minimum amount of water, and acidified to pH 1 with 2M hydrochloric acid. The resultant precipitate was extracted with ethyl acetate (3×75 ml) and the extracts were combined and dried (MgSO₄). The solvent was evaporated. The solid residue was triturated with ether, collected by filtration, washed with ether and dried in vacuo to give 4-fluoro-3,5-dimethylbenzenesulphinic acid (4.7 g). This was converted directly to its sodium salt by addition to a solution of sodium methoxide (1 equivalent) in methanol and evaporation of the solution.

Nitromethane (2.7 ml, 50 mmol) was added dropwise, at 0° C., to a solution of potassium t-butoxide (2.5 g, 22.3 mmol) in DMF (100 ml) with stirring. When the addition was complete, stirring was continued for an additional 30 minutes at 0° C. The previously prepared sample of sodium 4-fluoro-3,5-dimethylbenzenesulphinate was added in one portion, followed immediately by iodine (2.88 g; 11.3 mmol). The cooling bath was removed and the mixture was stirred for 3 hours. A concentrated solution of aqueous sodium sulphite was added to partially decolourise the reaction mixture. The mixture was then poured into water (500 ml) and acidified to pH 1 with 2H hydrochloric acid. The precipitated solid was collected by filtration, washed with water, and dissolved in ethyl acetate (100 ml). The solution was washed with water, then with brine, dried (MgSO₄) and the solvent was evaporated. The pale yellow solid obtained was purified by MPLC, eluting with ethyl acetate/hexane (1:10 v/v, gradually increasing to 1:5 v/v), to give (4-fluoro-3,5-dimethylphenylsulphonyl)nitromethane as a colourless solid (0.6 g), m.p. 131°–132° C. (recrystallised from ethyl acetate/hexane); microanalysis found: C 43.7; H 4.1; N 5.6%; C₉H₁₀FNO₄S requires: C 43.7; H 4.1; N 5.7%.

EXAMPLES 22-25

Using an analogous procedure to that described in Example 21, but starting from the appropriate sodium sulphinate of formula IV (M=sodium), there were obtained the following compounds of formula I in yields of 4 to 12%:

| Example | Q | m.p. (°C.) | recrystallisation solvent(s) |
|---|---|---|---|
| 22 | 4-methoxyphenyl | 84-85 | ethyl acetate/hexane |
| 23 | 3-acetamido-4-methoxyphenyl | 181-182 | ethyl acetate/ethanol |
| 24 | 4-acetamido-2,5-dimethylphenyl | 185-186 | ethyl acetate/hexane |
| 25 | 2,5-dimethylphenyl | 55-56 | * |

[*Purified by MPLC using dichloromethane/hexane (1:1 v/v)].

The sulphinates of formula IV may be obtained by analogy with the procedure of Example 21 from the appropriate sulphonyl chloride, which may be obtained, for example, by chlorosulphonation of the appropriate compound of the formula Q.H.

EXAMPLE 26

(4-Acetamidophenylsulphonyl)nitromethane (obtained as described in J Het. Chem., 1977, 14, 1415) (10.0 g, 38.8 mmol) was added in one portion to a boiling mixture of concentrated hydrochloric acid (20 ml), water (100 ml) and ethanol (40 ml). The mixture was stirred at reflux until a clear solution formed (about 20 minutes) and then for a further 5 mins. The hot reaction mixture was poured into an excess of ice-cold saturated sodium bicarbonate solution and then extracted with ethyl acetate. The combined extracts were washed with brine, dried (MgSO4) and the solvent was removed by evaporation. There was thus obtained (4 aminophenylsulphonyl)nitromethane as a pale yellow solid (5.2 g, 62% yield), m.p. 132°-133° C., microanalysis, found: C, 39.2; H, 3.8: N, 12.9%; $C_7H_8N_2O_4S$ requires: C, 38.9; H, 3.7; N, 12.95%.

EXAMPLE 27

(4-Aminophenylsulphonyl)nitromethane (0.96 g, 4.44 mmol) was suspended in ether (50 ml). Acetic formic anhydride (1.0 g, 11.36 mmol) was added dropwise and the reaction mixture was stirred for 16 hours. The white precipitate was collected by filtration and triturated with ether (50 ml). There was thus obtained (4-formamidophenylsulphonyl)nitromethane (0.98 g, 90% yield), m.p. 192°-193° C. (after recrystallisation from aqueous methanol); microanalysis, found: C, 39.3; H, 3.1; N, 11.4%; $C_8H_8N_2O_5S$ requires: C, 39.3; H, 3.3; N, 11.5%.

EXAMPLE 28

(4-Aminophenylsulphonyl)nitromethane (0.86 g, 4 mmol) was dissolved in dry tetrahydrofuran (20 ml) under an atmosphere of argon. Triethylamine (0.61 g, 6 mmol) was added, followed by benzoyl chloride (0.62 g, 4.4 mmol). The mixture was then stirred for 2 hours. The precipitated triethylamine hydrochloride was removed by filtration and the filtrate concentrated in vacuo. The orange oil obtained was purified by MPLC, eluting with dichloromethane/ethyl acetate (9:1 v/v) to give (4-benzamidophenylsulphonyl)nitromethane (0.25 g. 20% yield) as a solid, m.p. 211°-212° C.; microanalysis, found: C, 52.3; H, 3.7; N, 8.4%; $C_{14}H_{12}N_2O_5S$ requires: C, 52.5; H, 3.75; N, 8.75%.

EXAMPLES 29-31

Using a similar procedure to that described in Example 13, but starting from the appropriate thioether of formula VII, the following compounds were obtained. (Example 29):

(3-Fluorophenylsulphonyl)nitromethane, as a solid, m.p. 68°-69° C.: [purified by MPLC using ethyl acetate/hexane (1:10 v/v)]; microanalysis, found: C, 38.5; H, 2.76; N, 6.39%; $C_7H_6FNO_4S$ requires: C, 38.36; H, 2.8; N, 6.2%, in 12% yield, starting from (3-fluorophenylthio)nitromethane [itself isolated as an oil having a satisfactory NMR spectrum (200 MHz, CDCl3): 5.48 (s, 2H), 7.0-7.43 (m, 4 aromatic H), after purification by MPLC using ethyl acetate/hexane (1:10 v/v)];

(Example 30):

(2-Chloro-3-methylphenylsulphonyl)nitromethane, as a solid, m.p. 95°-97° C.; [purified by MPLC using ethyl acetate/hexane (1:10 v/v)]; microanalysis, found: C, 38.0; H, 3.2; N, 5.1%; $C_8H_8ClNO_4.1/4 H_2O$, requires: C, 37.8; H, 3.4; N, 5.5%; in 25% yield, starting from (2-chloro-3-methylphenylthio)nitromethane [itself isolated as an oil having a satisfactory NMR spectrum after purification by MPLC using ethyl acetate/hexane (1:10 v/v)];

(Example 31):

[4-(N,N-dipropylsulphamoyl)phenylsulphonyl]nitromethane as a solid, m.p. 103°-104° C.; [purified by recrystallisation using ethyl acetate/hexane]; microanalysis, found: C, 43.2; H, 5.6; N, 7.5%; $C_{13}H_{20}N_2O_6S_2$ requires: C, 42.9; H, 5.5; N, 7.7%; in 51% yield, starting from [4-(N,N-dipropylsulphamoyl)phenylthio]nitromethane, [itself isolated as a solid having a satisfactory NMR spectrum (200 MHz, d6DMSO): 0.7-0.9 (t, 6H), 1.35-1.6 (m, 6H), 2.95-3.1 (t, 4H), 6.25 (s, 2H), 7.6-7.8 (m, 4 aromatic H), after purification by MPLC using ethyl acetate/hexane (1:10 v/v)];

EXAMPLE 32

A 1.55M solution of butyllithium (40 ml, 62 mmol) was added dropwise to a stirred solution of (4-bromophenylsulphonyl)nitromethane (A) (5.6 g, 20 mmol) in anhydrous tetrahydrofuran (250 ml) maintained at −65° to −70° C. under an atmosphere of Argon. When the addition was complete, the mixture was stirred for 20 minutes at −70° C. The mixture was poured into hexane containing solid carbon dioxide and allowed to rise to ambient temperature. The mixture was acidified to pH 2 with 2M hydrochloric acid, allowed to stand for one hour, and was then extracted with ethyl acetate. The extracts were combined, dried (MgSO4) and the solvent was removed by evaporation. The residue was triturated with ether and the resultant colourless solid collected by filtration. There was thus obtained (4-carboxyphenylsulphonyl)nitromethane (0.28 g) m.p. 213°-215° C. (recrystallised from ethyl acetate/hexane); microanalysis, found: C, 39.5, H, 2.9; N, 5.5%; $C_8H_7NO_6S$ requires: C, 39.2; H, 2.9; N, 5.7%.

The starting material (A) was itself obtained as a solid m.p. 163 164° C. (recrystallised from ethyl acetate/hexane) using an analogous procedure to that described in Example 3 from sodium 4-t bromobenzenesulphinate.

EXAMPLE 33

Thionyl chloride (0.33 ml, 4.5 mmol) was added dropwise to a stirred solution of (4-carboxyphenylsulphonyl)nitromethane (1.0 g, 4 mmol) in methanol (12 ml) cooled in an ice-salt bath. The mixture was stirred for 16 hours at ambient temperature and the solvent evaporated. The residue was purified by MPLC eluting with dichloromethane, gradually increasing to methanol/dichloromethane (1:50 v/v), to give (4-methoxycarbonylphenylsulphonyl)nitromethane (0.45 g), m.p. 106°–108° C.; microanalysis, found: C, 41.8; H, 3.5; N, 5.2%; $C_9H_9NO_6S$ requires: C, 41.7; H, 3.5; N, 5.4%.

EXAMPLE 34

Thionyl chloride (10 ml, 13.7 mmol) was added to (4-carboxyphenylsulphonyl)nitromethane (1 g, 4 mmol) and the mixture was refluxed for 15 minutes with stirring. The solution was evaporated and toluene (10 ml) was added. The solution was evaporated and the residual oil was dissolved in chloroform (10 ml). The solution was cooled to 0° C. A solution of dimethylamine in chloroform was added dropwise to the stirred mixture until there was an excess of dimethylamine present. The mixture was stirred for 15 minutes and evaporated. The residue was acidified with 2M hydrochloric acid and extracted with ethyl acetate. The combined extracts were dried (MgSO$_4$) and solvent was removed by evaporation. The residual pale yellow solid was recrystalised from ethyl acetate to give [4-(N,N-dimethylcarbamoylphenylsulphonyl)]nitromethane (0.4 g) m.p. 144°–146° C.; microanalysis, found: C, 44.0; H, 4.4; N, 10.1%; $C_{10}H_{12}N_2O_5S$ requires: C, 44.1; H, 4.4; N, 10.3%.

EXAMPLE 35

Borane-methyl sulphide complex (0.1 ml, 1 mmol) was added to a solution of (4-carboxyphenylsulphonyl)nitromethane (0.25 g, 1 mmol) in anhydrous tetrahydrofuran (5 ml) and the mixture was stirred for 2 hours. The mixture was acidified with 2M hydrochloric acid to pH 1 and extracted with ethyl acetate. The combined extracts were dried (MgSO$_4$) and the solvent was removed by evaporation. The residue was purified by MPLC eluting with methanol/dichloromethane (1:50 v/v) to give (4-hydroxymethylphenylsulphonyl)nitromethane (0.06 g) m.p. 73°–75° C.; microanalysis, found: C, 41.6; H, 3.9; N, 5.8%; $C_8H_9NO_5S$ requires: C, 41.6; H, 3.9; N, 6.1%.

EXAMPLE 36

(4-Formamidophenylsulphonyl)nitromethane (1.70 g, 7.0 mmol) was suspended in dry tetrahydrofuran (5.0 ml) at 0° C. under an atmosphere of argon. Borane-methylsulphide complex (1.75 ml, 17.5 mmol) was added dropwise over a period of 30 minutes. The reaction mixture was allowed to attain room temperature. The mixture was carefully acidified with 2M hydrochloric acid and extracted three times with ether. The combined extracts were washed with brine, dried (MgSO$_4$) and the solvent removed by evaporation. The yellow solid obtained was purified by MPLC, eluting with ethyl acetate/hexane (1:1 v/v) to give [4 (N-methylaminophenylsulphonyl)]nitromethane as a solid, (0.43 g, 27% yield) m.p. 123–°124° C. [recrystallised from ethyl acetate/hexane (1:4 v/v)]; microanalysis, found: C, 41.8; H, 4.2; N, 11.8%; $C_8H_{10}N_2O_4S$ requires: C, 41.7; H, 4.35; N, 12.1%.

EXAMPLE 37

Sodium borohydride (0.76 g, 20 mmol) was added in portions to a solution of (4-aminophenylsulphonyl)nitromethane (1.08 g, 5 mmol) in acetic acid (20 ml). When vigorous effervescence had subsided, the mixture was warmed at 60° C. for 16 hours. The solvent was removed by evaporation. The crystalline residue was purified by MPLC eluting with ethyl acetate/hexane (3:10 v/v) to give an oil. The oil was triturated with hexane and the resultant solid collected by filtration. There was thus obtained [4-(N,N-diethylaminophenylsulphonyl)]nitromethane (0.37 g) m.p. 102°–103° C.; microanalysis, found: C, 48.7; H, 5.9; N, 10.2%; $C_{11}H_{16}N_2O_4S$ requires: C, 48.5; H, 5.9; N, 10.3%.

EXAMPLE 38

(4-Aminophenylsulphonyl)nitromethane (1.62 g, 7.5 mmol) was dissolved in dry tetrahydrofuran (35 ml) under an atmosphere of argon. Triethylamine (1.14 g, 11.25 mmol) was added, followed by butyryl chloride (0.88 g, 8.25 mmol). The mixture was stirred for 2 hours. The precipitated triethylamine hydrochloride was removed by filtration and the filtrate concentrated in vacuo. The brown oil obtained was purified by MPLC, eluting with dichloromethane/methanol (99:1 v/v) to give (4-butyramidophenylsulphonyl)nitromethane (0.16 g, 7.5% yield) as a solid, m.p. 155 156° C.; microanalysis, found: C, 45.8; H, 4.8; N, 9.6%; $C_{11}H_{14}N_2O_5S$ requires: C, 46.1; H, 4.9; N, 9.8%.

EXAMPLE 39

(4-Carboxyphenylsulphonyl)nitromethane (1.7 g, 6.9 mmol) was added to thionyl chloride (17 ml) and the mixture was heated at reflux for fifteen minutes. The resultant yellow solution was evaporated and dry toluene (20 ml) was added. The mixture was evaporated and the residual oil was dissolved is dioxan (4 ml). The solution was added slowly to ice-cold ammonia solution (density, 0.91 g/ml; 20 ml) with stirring. When the addition was complete, the mixture was stirred for 30 minutes at 0° C. The mixture was acidified to pH 2 by addition of 2M hydrochloric acid and extracted with ethyl acetate. The combined extracts were dried (MgSO$_4$) and the solvent was evaporated. The solid residue was purified by MPLC, eluting with methanol/dichloromethane (1:20 v/v, gradually increasing to 1:5 v/v) to give (4-carboxamidophenylsulphonyl)nitromethane (0.5 g) m.p. 174°–176° C.; microanalysis, found: C, 39.5; H, 3.2; N, 11.0%; $C_8H_8N_2O_5S$ requires: C 39.3; H, 3.3; N, 11.5%.

EXAMPLE 40

Phosphorus oxychloride (5 ml) was added to (4-carboxamidophenylsulphonyl)nitromethane (0.75 g, 3 mmol) and the stirred mixture was heated at reflux for 40 minutes. The mixture was allowed to cool and excess phosphorus oxychloride was removed by evaporation. Ice was added to the residue and the mixture was allowed to attain ambient temperature. The mixture was extracted with ethyl acetate and the combined extracts dried (MgSO$_4$). The solvent was evaporated to give (4-cyanophenyl-sulphonyl)nitromethane (0.5 g), m.p. 158°–160° C. (after recrystallisation from ethyl acetate/hexane): microanalysis, found: C, 42.5; H, 2.7; N, 11.9%; $C_8H_6N_2O_4S$ requires: C, 42.5; H, 2.7; N, 12.4%.

EXAMPLE 41

Using an analogous procedure to that described in Example 21, there was obtained (4-methylthiophenylsulphonyl)nitromethane, as a solid, m.p. 98°–100° C. (after recrystallisation from ethyl acetate/hexane); microanalysis, found: C, 39.3; H, 3.6; N, 5.5%; $C_8H_9NO_4S_2$ requires: C, 38.9; H, 3.6; N, 5.7%, in 7% yield, starting from 4-methylthiobenzenesulphinic acid [itself obtained as described in J. C. S., 1948, 604–605].

EXAMPLE 42

A solution of potassium peroxymonosulphate ['Oxone' (trade mark); 4.17 g, 6.75 mmol] in water (12.5 ml) was added in one portion to a vigorously stirred solution of (4 hydroxyphenylthio)nitromethane (A) (850 mg, 4.58 mmol) in 1,2-dimethoxyethane (25 ml). The mixture was stirred overnight. The mixture was added to water (400 ml) and extracted with ethyl acetate. The combined extracts were washed with brine, dried ($MgSO_4$), and the solvent was evaporated. The residual solid was recrystallised from chloroform to give (4-hydroxyphenylsulphonyl)nitromethane, as a white solid (373 mg), m.p. 93°–95° C., microanalysis, found: C,38.7; H, 3.2; N, 6.2%; $C_7H_7NO_5S$ requires: C, 38.7; H, 3.2; N, 6.45%.

The starting material (A) was obtained as follows:

A solution of (4-hydroxyphenylthio)acetic acid (obtained as described in British Patent 818783) (0.5 g, 2.72 mmol) in anhydrous tetrahydrofuran (20 ml) was added dropwise to a stirred mixture of a 1.6M solution of butyllithium in hexane (5.35 ml, 8.56 mmol) and anhydrous tetrahydrofuran (20 ml) maintained at −40° to −45° C. under an atmosphere of argon. When the addition was complete, the mixture was stirred for one hour at −40° C. The mixture was allowed to warm to 0° C., and then cooled again to −40° C. Iso-amyl nitrate (1.08 g, 8.12 mmol) was added in one portion. The reaction mixture was stirred and the temperature was allowed to rise to ambient temperature overnight. The mixture was acidified to pH2 with 1.6M hydrochloric acid and was then stirred for one hour. Water (250 ml) was added and the mixture was extracted with ethyl acetate. The combined extracts were filtered through a phase-separating filter paper and the solvent was evaporated.

The residue was purified by chromatography on silica, eluting with methanol/dichloromethane (1:100 v/v) to give (4-hydroxyphenylthio)nitromethane (A) as an oil which crystallised (61 mg). NMR spectrum (200 MHz, $CDC_{13}$): 5.35(s,2H), 6.8(m,2 aromatic H), 7.42(m,2 aromatic H).

EXAMPLE 43

A solution of potassium permanganate in water (30 ml of a 3% w/v solution, 5.7 mmol) was added in one portion to a stirred solution of (4-methylthiophenylsulphonyl)nitromethane (1 g, 4 mmol) in acetic acid (30 ml). The mixture was stirred for 30 minutes, diluted with water (100 ml) and decolourised with sodium sulphite solution. The solid precipitate was collected by filtration, washed with water and air dried. There was thus obtained (4 methylsulphonylphenylsulphonyl)nitromethane (0.76 g) m.p. 220°–221° C. (after recrystallisation from ethyl acetate/hexane); microanalysis, found: C, 34.4; H, 3.2; N, 4.8%; $C_8H_9NO_6S_2$ requires: C, 34.4; H, 3.2; N, 5.0%.

EXAMPLE 44

A solution of potassium peroxymonosulphate ['Oxone' (trade mark); 0.86 g, 1.4 mmol] in water (10 ml) was added in one portion to a vigorously stirred solution of (4-methylthiophenylsulphonyl) nitromethane (0.54 g, 1.18 mmol) in 1,2-dimethoxyethane((10 ml) at 0° C. The mixture was stirred for 30 minutes at 0° C. and then diluted with water. The solid precipitate was collected by filtration, washed with water and air dried. There was thus obtained (4-methylsulphinylphenylsulphonyl)nitromethane, as a solid (0.24 g), m.p. 145°–146° C. (after recrystallisation from ethyl acetate/hexane); microanalysis, found: C, 36.7; H, 3.4; N, 5.0%; $C_8H_9NO_5S_2$ requires: C, 36.5; H, 3.4; N, 5.3%.

EXAMPLE 45

Using a similar procedure to that described in Example 13, there was obtained (3,4-methylenedioxyphenylsulphonyl)nitromethane, as a solid, m.p. 131°–132° C. [purified by MPLC using ethyl acetate/hexane (1:10 v/v)]; microanalysis, found: C, 39.2; H, 2.9; N, 5.7%; $C_8H_7NO_6S$ requires; C, 39.2; H, 2.9; N, 5.7%; in 3.6% yield, starting from (3,4-methylenedioxyphenylthio)nitromethane (A) [itself isolated as an oil having a satisfactory NMR spectrum (200 MHz, $CDCl_3$): 6.2–7.1(m,3H, 6.0(s,2H), 5.35(s,2H), after purification by MPLC using ethyl acetate/hexane (1.20 v/v)].

The starting thioether (A) was itself obtained using an analogous procedure to that described in Example 13 from 3,4-methylenedioxyphenylthioacetic acid, which was obtained as follows:

(i) Lead thiocyanate (45 g, 139 mmol) was added in portions to a stirred solution of chlorine (20.3 g, 290 mmol) in anhydrous acetic acid (600 ml) under an atmosphere of argon. The mixture was stirred for 15 minutes. 1,2-Methylenedioxybenzene (35 g, 286 mmol) was added in one portion. The mixture was stirred for 1 hour and then filtered. The filtrate was added to ice-water (3.5 liters). The precipitated solid was collected by filtration, dissolved in ethyl acetate and dried ($MgSO_4$). The solvent was removed by evaporation to give 3,4-methylenedioxyphenyl thiocyanate as a pale green oil (40.3 g, 79% yield). The oil solidified and was used without further purification or characterisation.

(ii) Sodium borohydride (8.4 g, 220 mmol) was added in portions to a stirred solution of 3,4-methylenedioxyphenyl thiocyanate (35.9 g, 200 mmol) in ethanol (1.06 liters) under an atmosphere of argon during 10 minutes. The mixture was stirred for a further 10 minutes and was then heated at reflux for 10 minutes. The mixture was allowed to cool to ambient temperature. A solution of sodium hydroxide (13 g) in ethanol (250 ml) was added to the stirred mixture over one minute, followed by sodium chloroacetate (23.3 g, 200 mmol). The mixture was stirred for 16 hours. The mixture was acidified with 2M hydrochloric acid and extracted with ethyl acetate. The combined extracts were then extracted with a saturated aqueous solution of sodium hydrogen carbonate. The aqueous extract was acidified with 2M hydrochloric acid and extracted with ethyl acetate. The combined extracts were dried ($MgSO_4$), and the solvent was removed by evaporation to yield 3,4-methylenedioxypheylthioacetic acid, as a colourless solid (18 g, 42% yield), NMR spectrum (200 MHz, $CDCl_3$): 3.57 (s, 2H), 5.98 (s, 2H), 6.7–7.1 (m,3 aromatic H), 9.81 (s,1H).

EXAMPLE 46

Using a similar procedure to that described in Example 20, except that oxidation was carried out at ambient temperature for 5 minutes, there was obtained (3 chloro-2-methylphenylsulphonyl)nitromethane, as a solid, m.p. 78°–79° C., in 19% yield; microanalysis, found: C, 38.5; H, 3.2; N, 5.3%; $C_8H_8ClNO_4S$ requires C, 38.5; H, 3.2; N, 5.6%; starting from (3-chloro-2-methylphenylsulphinyl)nitromethane, itself obtained from (3-chloro- 2-methylphenylthio)nitromethane (A) by an analogous procedure to that described in Example 20.

The starting thioether (A) was obtained from (3-chloro-2-methylphenyl)thioacetic acid, itself obtained from 3-chloro-2-methylbenzenethiol, in both cases using analogous procedures to those described in Example 13.

EXAMPLE 47

Using a similar procedure to that described in Example 13 except that the oxidation was carried out at 60° C. for 6 hours and 1,2-dimethoxyethane was used instead of methanol, (4-phenoxyphenylsulphonyl)nitromethane was obtained as a solid, m.p. 118°–120° C.; microanalysis, found: C, 53.4; H, 3.8; N, 4.7%; $C_{13}H_{11}NO_5S$ requires; C, 53.2; H, 3.8; N, 4.8%; (purified by recrystallisation from toluene); in 38% yield, starting from (4-phenoxyphenylthio)nitromethane (A) [itself isolated as an oil having a satisfactory NMR spectrum (200 MHz, $CDCl_3$): 5.38 (s, 2H), 6.93 7.33 (m,9 aromatic H), after purification by flash chromatography on silica (Merck Kieselgel Art. 9385) using ether/hexane (1:4 v/v)];

The starting thioether (A) was obtained from the corresponding thioacetic acid, by analogy with the procedure in Example 13, itself obtained as follows:

4-Phenoxyaniline (30 g, 162 mmol) was added in portions to a stirred solution of 98% w/v sulphuric acid (93 ml) in water (480 ml). The mixture was heated at 80° C. for 30 minutes and then cooled to 0°–5° C. A solution of sodium nitrite (13.5 g, 196 mmol) in water (60 ml) was added dropwise and the mixture was stirred for 45 minutes at 0° C. The excess nitrous acid was destroyed with sulphamic acid. The solution was added to a stirred mixture of 2-mercaptoacetic acid (14.7 ml, 211 mmol), basic copper carbonate (10.8 g, 49 mmol) and acetone (180 ml) at 0° C. The mixture was warmed to ambient temperature. After 1 hour ethyl acetate (200 ml) was added and the insoluble material was removed by filtration. The filtrate was extracted with ethyl acetate. The combined extracts were then extracted with a saturated solution of sodium hydrogen carbonate. The combined aqueous extracts were acidified to pH 2 by the addition of 2M hydrochloric acid and extracted with ethyl acetate. The combined extracts were washed with brine and dried ($MgSO_4$). The solvent was removed by evaporation to give 4-phenoxyphenylthioacetic acid as an oil (12.3 g) having a satisfactory NMR spectrum (200 MHz, $CDCl_3$); 3.61 (s,2H), 6.93–7.46 (m,9 aromatic H), after purification by flash chromatography on silica (Merck Kieselgel Art 9385) using ethyl acetate/dichloromethane (1:1 v/v).

EXAMPLE 48

Using a similar procedure to that described in Example 13, there was obtained (4-methoxy-1-naphthylsulphonyl)nitromethane, as a white solid, m.p. 109°–110° C. (after recrystallisation from methanol); microanalysis, found: C, 51.1; H, 3.9; N, 4.9%; $C_{12}H_{11}NO_5S$ requires: C, 51.3; H, 3.9; N, 5.0%, in 21% yield, starting from (4-methoxy-1-naphthylthio)nitromethane (itself isolated as an oil), using an analogous procedure to that described in Example 13, and starting from 4-methoxy-1-naphthylthioacetic acid, itself obtained as follows:

(i) A solution of thiocyanogen (69.6 mmol) in methyl acetate (150 ml) (obtained as described by Y Tamura et al in Tetrahedron Letters, 1977, 4417) was added to a solution of 1-methoxynaphthalene (10.92 g, 69.3 mmol) in methyl acetate (80 ml) at 0° C. The resultant yellow solution was stirred for 16 hours at ambient temperature. A saturated solution of sodium bicarbonate (100 ml) was added and the mixture was filtered through diatomaceous earth. The organic phase was separated, and dried ($N_2SO_4$). The solvent was removed by evaporation to give 4-methoxy-1-naphthyl thiocyanate (A), as a white solid, (7.5 g), m.p. 100°–102° C. [after recrystallisation from petroleum ether (b.p. 80°–100° C.)].

(ii) Sodium borohydride (1.7 g, 45 mmol) was added to a suspension of A (7.5 g, 34.9 mmol) in ethanol (150 ml). Argon was passed through the mixture. The mixture was stirred for 30 minutes and then heated at 80° C. for 30 minutes. A solution of potassium hydroxide (5.04 g, 90 mmol) in ethanol (60 ml) was added to the stirred mixture followed by chloroacetic acid (4.25 g, 450 mmol). The mixture was stirred for 30 minutes and then heated at 80° C. for 30 minutes. The reaction mixture was allowed to cool and then added to water (1 liter) and extracted with ether. The aqueous phase was acidified to pH 2 by the addition of 2M hydrochloric acid and extracted with ethyl acetate. The combined extracts were dried ($N_2SO_4$) and the solvent was removed by evaporation to give 4-methoxy-1-naphthylthioacetic acid (5.38 g) m.p. 114°–115° C., [after recrystallisation from ethanol/water (1:1 v/v)].

EXAMPLES 49–51

Using a similar procedure to that described in Example 3, the following compounds of formula I were obtained in yields 1–27% and had satisfactory elemental analyses and NMR spectra:

| Example | Q | m.p. | recrystallisation solvent(s) |
|---|---|---|---|
| 49 | 4-propylphenyl | 92–94 | ethanol |
| 50* | 3-chloro-4-fluorophenyl | 57–60 | toluene/hexane |
| 51 | 4-allyloxyphenyl | 88–90 | ethanol |

[*This compound was obtained from the acidified reation mixture by an analogous procedure to that described for Example 9].

The necessary sodium sulphinate salts of formula IV were made using an analogous procedure to that described for Example 3. However, the sulphinate starting material for Example 51, was obtained as described for Example 8.

The required starting sulphonyl chlorides were either commercially available or obtained by standard methods, well known in the art, as referred to in Examples 4–12. The sulphonyl chloride for Example 51 was obtained using the procedure described in Helvetica Chimica Acta, 1956, 39, 1579–1586.

EXAMPLE 52

A solution of peracetic acid in acetic acid (32 wt%, 4 ml, 19 mmol) was added dropwise to an efficiently stirred solution of (9-phenanthrylthio)nitromethane (A) (1 g, 3.7 mmol) in chloroform (50 ml). The mixture was stirred for 20 hours and then diluted with water (20 ml). The organic phase was separated and washed with an aqueous solution of sodium metabisulphite, then with brine, and dried ($N_2SO_4$). The solvent was removed by evaporation to give a yellow solid. This was purified by flash chromatography on silica (Merck Kieselgel Art. 7736) eluting with toluene to give (9-phenanthrylsulphonyl)nitromethane, as a white crystalline solid (180 mg, 16% yield) m.p. 165°–166° C., (after recrystallisation from toluene); microanalysis, found: C, 59.7; H, 3.7; N, 4.6%; $C_{15}H_{11}NO_4S$ requires: C, 59.8; H, 3.7; N, 4.7%

The starting thioether (A) was itself obtained as a solid, m.p. 85°-86° C. (after recrystallisation from cyclohexane); microanalysis, found: C, 67.3; H, 4.2; N, 5.0% $C_{15}H_{11}NO_2S$ requires: C, 66.9; H, 4.1; N, 5.2%; using an analogous procedure to that described in Example 13 starting from 9-phenanthrylthioacetic acid, itself obtained as described by Wynberg et al in JACS 1967, 89, 3487.

EXAMPLE 53

Using a similar procedure to that described in Example 42, there was obtained [3 (1-hydroxyethyl)phenylsulphonyl]nitromethane as an oil, in 87% yield, [after purification by chromatography on silica using ethyl acetate/toluene (1:10 v/v)] having a satisfactory NMR spectrum (200 MHz, CDCl$_3$): 1.51(d,3H), 2.43(s,1H), 5.00(q,1H), 5.64(s,2H), 7.55 8.00 (m,4 aromatic H), and mass spectrum (chemical ionisation) m/e 263 $(M+NH_4)^+$, starting from [3-(1-hydroxyethyl)phenylthio]nitromethane (A).

The thioether (A) was obtained as an oil from 3-(1-hydroxyethyl)phenylthioacetic acid by analogy with the procedure described in Example 42, itself obtained as a white solid, m.p. 83°-84° C., from 1-(3-aminophenyl)ethanol by analogy with the procedure described in Example 47.

EXAMPLE 54

A solution of [3-(1-hydroxyethyl)phenylsulphonyl]-nitromethane (1.10 g, 4.5 mmol) in dichloromethane (10 ml) was added to a vigorously stirred suspension of pyridinium chlorochromate (1.45 g, 6.7 mmol) in dichloromethane (10 ml). The mixture was stirred for 2 hours. Ethyl acetate (100 ml) was added and the solvent was decanted. The black residue was washed twice with ethyl acetate. The extracts and the decanted solution were combined and filtered through magnesium silicate ['Florisil' (trade mark)]. The solvent was evaporated. The residual yellow solid was recrystallised from toluene to give (3-acetylphenylsulphonyl)nitromethane, as a solid, (0.67 g), m.p. 99°-100° C., microanalysis, found: c, 44.7; H, 3.8; N, 5.7%; $C_9H_9NO_5S$ requires: C, 44.4; H, 3.7; N, 5.8%.

EXAMPLE 55

Using analogous procedures to those described in Example 20 there was thus obtained (pentamethylphenylsulphonyl)nitromethane, as a solid m.p. 146°-147° C.; [purified by MPLC using dichloromethane/hexane (2:1 v/v)], microanalysis, found: C, 53.4; H, 6.5; N, 5.2%; $C_{12}H_{17}O_4NS$ requires: C, 53.1; H, 6.3; N, 5.2%; in 10.5% yield, starting from (pentamethylphenylsulphinyl)nitromethane [itself isolated as a solid having a satisfactory NMR spectrum (200 MHz, CDCl$_3$): 2.15-2.25 (m, 9H), 2.5-2.63(m, 6H),5.35-5.83(q,2H) after recrystallisation from ethyl acetate/hexane]; in 79% yield, starting from (pentamethylphenylthio)nitromethane(A). The thioether (A) was isolated as an oil having a satisfactory NMR spectrum (200 MHz, CDCl$_3$); 2.1-2.2(s, 9H), 2.4-2.5(m, 6H), 5.55(s,2H), [after purification by chromatography on silica using hexane] starting from pentamethylphenylthioacetic acid, using an analogous procedure to that described in Example 13.

The necessary thioacetic acid of formula VII was obtained as follows:

A 1M solution of lithium aluminium hydride in ether (235 ml) was added dropwise to a stirred solution of pentamethylbenzenesulphonyl chloride (25 g. 101.4 mmol) in anhydrous ether (300 ml) under an atmosphere of argon. When the addition was complete, the reaction mixture was heated at reflux for four hours and then allowed to cool to ambient temperature. Water was added dropwise until the evolution of gas had ceased. A 10% aqueous solution of sulphuric acid (150 ml) was added to dissolve the lithium salts. Toluene (200 ml) was added and the organic phase was separated, washed with water, brine, and dried (MgSO$_4$). 1N Sodium hydroxide solution (101.4 ml, 101.4 mmol) was added, followed by sodium chloroacetate (11.8 g, 101.4 mmol) with stirring. The mixture was stirred for 24 hours. The reaction mixture was poured into water (1 liter) and acidified with 2M hydrochloric acid. The aqueous mixture was extracted with ethyl acetate. The extracts were combined, washed with water, brine and dried (MgSO$_4$). The solvent was removed by evaporation to give pentamethylphenylthioacetic acid, as a cream coloured solid (16 g); microanalysis, found: C, 65.5; H, 7.6%; $C_{13}H_{18}O_2S$ requires C, 65.55; H, 7.56%.

EXAMPLE 56 m-Chloroperbenzoic acid (80-85%; 1.27 g) was added in portions to a solution of 2 methyl-2-[4-(nitromethylthio)phenyl]1,3 dioxolane (A) (2.7 g) in chloroform (10 ml) at 0° C. The mixture was filtered after 3-hours and the clear filtrate was washed with a 20% aqueous solution of sodium metabisulphite (2×15 ml). The organic phase was dried and the solvent was removed by evaporation to give a white solid. The solid was dissolved in ethanol (5 ml) and 2M hydrochloric acid (2 ml) was added. The solution was stirred for 3 hours and then concentrated in vacuo. The residue was diluted with water and extracted with chloroform (2×10 ml). The extracts were combined and the solvent was removed by evaporation. The white solid obtained was purified by chromatography on silica eluting with ethyl acetate/hexane (1:4 v/v) to give (4 acetylphenylsulphonyl) nitromethane, as a solid (180mg), m.p. 94°-95° C. [after recrystallisation from methanol/water (2:1 v/v)]; microanalysis, found: C, 44.8; H, 3.7, N, 5.3%; $C_9H_9NO_5S$ requires: C, 44.4; H, 3.7; N, 5.8%.

The starting material (A) was obtained as follows:

(i) A solution of 4-acetylphenylthioacetic acid (8.4 g, 40 mmol) (obtained as described by Walker and Leib in J. Org. Chem. 1963, 28, 3077-3082), ethylene glycol (4.96 g, 80 mmol) and a catalytic quantity of p-toluenesulphonic acid in benzene (80 ml) was heated at reflux for 16 hours using a Dean and Stark apparatus. Water (1.5 ml, 80 mmol) was collected. The solvent was removed by evaporation to give an oil. Ethanol (30 ml) and 2N sodium hydroxide solution (1 equivalent) were added and the mixture was stirred for one hour. The mixture was concentrated in vacuo. The residue was diluted with water to give a volume of 80 ml. Ether (50 ml) was added and the mixture was stirred vigorously with cooling in ice. A 10% aqueous solution of citric acid was added to give a pH of 6.5. The mixture was extracted with ether (20×50 ml). The combined extracts were dried (N$_2$SO$_4$) and the solvent was removed by evaporation to give a white solid. Water was added to the solid and the mixture was stirred. The solid was collected by filtration and dried in vacuo over phosphorus pentoxide. There was thus obtained 4-(2-methyl-1,3-dioxolan-2-yl)phenylthioacetic acid (B) as a solid (5.2 g, 51% yield); NMR spectrum (200 MHz, d$_6$-DMSO):

1.49(s, 3H), 3.62(m, 2H), 3.72(s, 2H), 3.9(m, 2H), 7.25(m,4H).

(ii) A solution of lithium diisopropylamide was prepared by the addition of a 1.6M solution of butyllithium in hexane (9.23 ml, 15 mmol) to a stirred solution of diisopropylamine (2.07 ml, 15 mmol) in dry tetrahydrofuran (10 ml) at −70° C. under an atmosphere of argon. The solution was maintained at −70° C. for 30 minutes. A solution of B (1.5 g, 5.9 mmol) in tetrahydrofuran (10 ml) was added dropwise maintaining the temperature at −70° C. The mixture was maintained at −70° C. for one hour and then allowed to warm to −40° C. Isoamyl nitrate (2.37 ml, 17.7 mmol) was added slowly at −40° C. and the mixture was maintained at this temperature for one hour. The mixture was then allowed to warm to ambient temperature over 90 minutes. The reaction mixture was poured into a stirred mixture of ether (150 ml) and water (150 ml). A 10% aqueous solution of citric acid was added carefully to give a pH of 6.5 to 7.0. After one hour, the ether phase was separated, dried ($N_2SO_4$), and the solvent was removed by evaporation to give 2 methyl-2-[4-(nitromethylthio)-phenyl]1,3 dioxolane (A), as an oil (2.7 g), which had a satisfactory NMR spectrum.

EXAMPLE 57

Using an analogous procedure to that described in Example 13, there was obtained (2-isopropylphenylsulphonyl)nitromethane, as a solid m.p. 113°–114° C., in 28%.yield; [purified by MPLC using dichloromethane]; microanalysis, found: C, 49.3; H, 5.3; N, 5.8%; $C_{10}H_{13}NO_4S$ requires: C, 49.4; H, 5.4; N, 5.8%; starting from (2-isopropylphenylthio)nitromethane [itself isolated as an oil having a satisfactory NMR spectrum (20Q MHz, $CDCl_3$): 1.25(d,6H,), 3.57 (septet, 1H), 5.41(s,1H), 7.11–7.50(m,4 aromatic H), after purification by MPLC using dichloromethane]. The starting thioether was itself obtained from 2-isopropylphenylthioacetic acid, itself obtained from 2-isopropylbenzenethiol, in both cases using analogous procedures to those described in Example 13.

EXAMPLE 58

Using a similar procedure to that described in Example 20, there was obtained (2,3,5,6-tetrafluorophenylsulphonyl)nitromethane, as a solid, m.p. 86°–87° C.; [purified by chromatography on silica using ethylacetate/hexane (1:7 v/v)] microanalysis, found: C, 31.1; H, 1.2; N, 5.0%; $C_7H_3F_4NO_4S$ requires: C, 30.8; H, 1.1; N, 5.1%; in 19% yield, starting from (2,3,5,6 tetrafluorophenylsulphinyl)nitromethane, itself isolated as a crystalline solid m.p. 116°–117° C.; [purified by trituration with hexane]; microanalysis, found: C, 33.0; H, 1.3; N, 5.2%; $C_7H_3F_4NO_3S$ requires: C, 32.7; H, 1.2; N, 5.4%; in 63% yield; starting from (2,3,5,6-tetrafluorophenylthio)nitromethane (A).

The starting thioether (A) was obtained as an oil having a satisfactory NMR spectrum (200 MHz, $CDCl_3$): 5.46 (s, 2H), 7.11–7.30 (m, 1H), from 2,3,5,6-tetrafluorophenylthioacetic acid, itself obtained from 2,3,5,6-tetrafluorobenzenethiol, in both cases using analogous procedures to those described in Example 13.

EXAMPLE 59

Using an analogous procedure to that described in Example 20, there was obtained (7-chloro-1-naphthylsulphonyl)nitromethane, as a solid m.p. 136°–138° C., having a satisfactory NMR spectrum (200 MHz, $CDCl_3$) 5.76 (s, 2H), 7.65 (d, 1H), 7.67 (d, 1H), 7.99 (d, 1H), 8.24 (d, 1H), 8.39 (d, 1H), 8.64 (s, 1H), after purification by recrystallisation from ethyl acetate. in 27% yield, starting from (7- chloro-1-naphthylsulphinyl)nitromethane [itself isolated as a solid having a satisfactory NMR spectrum (200 MHz. $d_6$-DMSO) 5.97 (d, 1H), 6.26 (d, 1H), 7.65–8.33 (m, 6 aromatic H), after purification by recrystallisation from ethyl acetate/hexane]; in 35% yield, starting from (7-chloro-1-naphthylthio)nitromethane (A). The starting thioether (A) was obtained, as an oil [after purification by MPLC using ethyl acetate/hexane (1:10 v/v)]starting from 7-chloro-1-naphthylthioacetic acid, using an analogous procedure to that described for Example 13.

EXAMPLES 60–61

Using a similar procedure to that described in Example 20, the following compounds were obtained:
(Example 60): (2,3-dichlorophenylsulphonyl)nitromethane as a white solid, m.p. 130°–131° C. [purified by trituration with ether]; microanalysis, found: C,31.1; H,1.7; N,4.8%; $C_7H_5C_{l2}NO_4S$ requires: C,31.1; H,1.9; N,5.2%; in 12% yield, starting from (2,3-dichlorophenylsulphinyl)nitromethane, isolated as a solid, m.p. 102 103° C.; microanalysis, found: C,33.1; H,2.0; N,5.4%; $C_7H_5Cl_2NO_3S$ requires: C,33.1; H,2.0; N,5.5%; in 64% yield, starting from (2,3-dichlorophenylthio)nitromethane [itself isolated as an oil having a satisfactory NMR spectrum (200 MHz, $CDCl_3$): 5.54(s,2H), 7.24(t,1H), 7.44(d,1H), 7.48(d,1H,), after purification by flash chromatography on silica (Merck Kieselgel Art. 7736) using ethyl acetate/hexane (1:7 v/v)];
(Example 61):
(2 Chloro-4-fluorophenylsulphonyl)nitromethane as a white solid, m.p. 67° C. [purified by trituration with hexane]; microanalysis, found: C,33.0; H.1.8; N,5.2%; $C_7H_5ClFNO_4S$ requires: C,33.1; H,2.0; N.5.5%; in 47% yield, starting from (2-chloro-4-fluorophenylsulphinyl)-nitromethane, isolated as a solid, m.p. 73° C.; microanalysis, found: C,35.4; H,2.1; N,5.8%; $C_7H_5ClFNO_3S$ requires: C,35.4; H,2.1; N,5.9%; in 65% yield, starting from (2-chloro-4-fluorophenylthio) nitromethane [itself isolated as an oil having a satisfactory NMR spectrum (200 MHz, $CDCl_3$); 5.44(s,2H), 7.03(m,1H), 7.26(m,1H), 7.64(m,1H), after purification by MPLC using ethyl acetate/hexane (1:7 v/v)].

EXAMPLE 62

Using a similar procedure to that described in Example 17, except that the reaction was carried out for 3-hours at ambient temperature and then for a further 15 minutes at 50° C., there was obtained (2-trifluoromethylphenylsulphonyl)nitromethane as a white solid, m.p. 80° C. [purified by flash chromatography on silica (Merck Kieselgel Art. 7736) using ethyl acetate/hexane (1:10 v/v); microanalysis, found: C,36.2; H,2.5; N,4.9%; $C_8H_6F_3NO_4S$ requires: C,35.7; H,2.2; N,5.2%; in 22% yield, starting from (2-trifluoromethylphenylthio)nitromethane [itself isolated as an oil having a satisfactory NMR spectrum (200 MHz, $CDCl_3$); 5.45(s,2H), 7.46–7.83(m,4 aromatic H), after purification by flash chromatography on silica (Herck Kieselgel Art. 7736) using ethyl acetate/hexane (1:20 v/v)].

EXAMPLE 63

Using a similar procedure to that described in Example 17, except that the reaction mixture was stirred at 20° C. for 4-hours, there was obtained (2-fluorophenylsulphonyl)nitromethane as a white solid; m.p. 59° C. [purified by flash chromatography on silica (Merck Kieselgel Art. 7736) using ethyl acetate/hexane (1:10 v/v); microanalysis, found: C,38.8; H,2.8; N,6.2%; $C_7H_6FNO_4S$ requires: C,38.4; H,2.7; N,6.4%: in 33% yield, starting from (2-fluorophenylthio)nitromethane [itself isolated as an oil having a satisfactory NMR spectrum (200 MHz, $CDCl_3$): 5.44(s,2H), 7.15(m,2H), 7.38(m,1H). 7.53(m,1H), after purification by flash chromatography on silica (Merck Kieselgel Art. 7736) using ethyl acetate/hexane (1:10].

EXAMPLE 64

Using a similar procedure to that described in Example 17, except that the oxidation was carried out at ambient temperature for 30 minutes, there was obtained (2,6-dichlorophenylsulphonyl)nitromethane as a solid, m.p. 92 93° C.; [purified by MPLC using dichloromethane]; microanalysis, found: C,31.4; H,1. 8; N,5.1%; $C_7H_5Cl_2NO_4S$ requires: C,31.1; H,1. 8; N,5.2%; in 37% yield, starting from (2-chlorophenylthio)nitromethane [itself isolated as an oil having a satisfactory NMR spectrum (200 MHz, $CDCl_3$): 7.2-7.5 (m,3H), 5.43(s,2H), after purification by MPLC, eluting with ethyl acetate/hexane (1:20 v/v)].

EXAMPLE 65

Using a similar procedure to that described in Example 17, except that 3-equivalents of potassium permanganate were added and the reaction was allowed to proceed for 2 hours at ambient temperature, there was obtained (2-chlorophenylsulphonyl)nitromethane as a solid, m.p. 84°-85° C. [purified by MPLC using dichloromethane]; microanalysis, found: C,35.7; H,2.6; N,6.2%; $C_7H_6ClNO_4S$ requires: C,35.7; H,2.6; N,5.9%; in 3% yield, starting from (2-chlorophenylthio)nitromethane [itself isolated as an oil having a satisfactory NHR spectrum (200 MHz, $CDCl_3$): 7.0-8.2(m,5H), 5.51(s,2H), after purification by MPLC, eluting with ethyl acetate/hexane (1:10 v/v)].

EXAMPLE 66

Using a similar procedure to that described in Example 13, except that the reation was carried out at 55° C. for one hour, there was obtained (2,3,6-trimethylphenylsulphonyl)nitromethane as a solid, m.p. 92°-93° C. [purified by MPLC using dichloromethane]; microanalysis, found: C,49.4; M,5.4; N,5.7%; $C_{10}H_{13}NO_4S$ requires: C,49.4; H,5.4; N,5.8%; in 9% yield, starting from (2,3,6-trimethylphenylthio)nitromethane [itself isolated as an oil having a satisfactory NMR spectrum (200 MHz, $CDCl_3$); 7.0-7.1(m,2H), 5.25(s,2H), 2.48(s,6H), 2.28(s,3H), after purification by flash chromatography, eluting with ethyl acetate/hexane (1:10 v/v, gradually increasing to 3:5 v/v)].

EXAMPLE 67

Using a similar procedure to that described in Example 17, except that the oxidation was carried out for 18 hours at ambient temperature, there was obtained (2-methoxyphenylsulphonyl)nitromethane as a white solid, m.p. 71°-73° C. [after purification by MPLC eluting with ethyl acetate/hexane (1:9 v/v)]; in 37% yield; microanalysis, found: C,41.7; H,3.9; N,6.0%; $C_8H_9NO_5S$, requires; C,41.6; H,3.9: N,6.0%; starting from (2-methoxyphenylthio)nitromethane, [itself isolated as an oil having a satisfactory NMR spectrum (200 MHz, $CDCl_3$): 3.60(s,2H), 3.9(s,3H), 6.80-7.40(m,4H), after purification by chromatography on silica (Merck Kieselgel Art. 7736) using ethyl acetate/hexane (1:9 v/v)].

EXAMPLE 68

Using a similar procedure to that described in Example 17, except that the oxidation was carried out for 45 minutes at ambient temperature, there was obtained (2,4-dimethylphenylsulphonyl)nitromethane as a solid, m.p. 90°-92° C. [purified by trituration with ether]; microanalysis, found: C,47.1: H,4.8; N,5.9%; $C_9H_{11}NO_4S$ requires: C,47.2; H,4.8; N,6.1%; in 51% yield; starting from (2,4-dimethylphenylthio)nitromethane [itself isolated as an oil having a satisfactory NMR spectrum (200 MHz, $CDCl_3$): 2.35(s,3H), 2.45(s,3H), 5.35(s,2H), 7.0-7.4(m,3H), after purification by MPLC eluting with ethyl acetate/hexane (1:5 v/v)].

EXAMPLE 69

Using a similar procedure to that described in Example 17, except that the oxidation was carried out for 2 hours at ambient temperature, there was obtained (3,5-dimethylphenylsulphonyl) nitromethane as a solid, m.p. 64°-66° C. [purified by trituration with ether] having a satisfactory NMR spectrum (200 MHz, $CDCl_3$): 5.60(s,2H), 2.45(s,6H), 7.30-7.60(m,3H); in 17% yield: starting from (3,5 dimethylphenylthio)nitromethane [itself isolated as an oil having a satisfactory NMR spectrum (200 MHz, $CDCl_3$): 2.30(s,6H), 5.45(s,2H), 7.0-7.3(m,3H), after purification by MPLC eluting with ethyl acetate/hexane (1:5 v/v)].

The necessary thioethers of the formula VII used in Examples 60-69 were obtained from the corresponding thioacetic acids of the formula IX, themselves obtained from the appropriate thiols of the formula VIII, in both cases using procedures analogous to those described in Example 13.

The thiols of the formula VIII required for Examples 60 and 61 were prepared by conversion of the corresponding anilines into their sulphonyl chlorides, using an analogous procedure to that described in Org. Syn. Vol. 60, page 121, followed by reduction with zinc and sulphuric acid, using an analogous procedure to that described for the preparation of 2,4-dichlorobenzenethiol in J. Med. Chem. 1987, 30, 463.

2-Trifluoromethylphenylthioacetic acid was prepared by an analogous procedure to that described in Example 47, but starting from 2-trifluoromethylaniline.

EXAMPLE 70

Using a similar procedure to that described in Example 1, except that an equimolar amount of sodium methoxide was used in place of potassium t-butoxide, there was obtained (4-acetamido-2,6-dimethylphenylsulphonyl)nitromethane as a solid, m.p. 179°-180° C. [purified by trituration with methanol]; microanalysis, found: C,46.2; H,5.0; N,9.7%; $C_{11}H_{14}N_2O_5S$ requires: C,46.15; H,4.9; N,9.8%; in 21% yield.

The starting sulphinic acid sodium salt was obtained in an analogous manner to that for the starting material in Example 1 but using 4-acetamido-2,6-dimethylbenzenesulphonyl chloride [itself obtained by acetylation of 3,5-dimethylaniline, followed by chlorosulphonation, using conventional procedures].

EXAMPLE 71

Using a similar procedure to that described in Example 26, there was obtained (4-amino-2,6-dimethylphenyl)sulphonyl)nitromethane, as a solid, m.p. 132°-133° C. [after recrystallisation from ethanol]; microanalysis, found: C,44.5; H,4.9; N,11.6%; C9H12N2O4S requires: C,44.3; H,4.9; N,11.5%; in 73% yield; starting from (4-acetamido-2,6-dimethylphenylsulphonyl)nitromethane.

EXAMPLE 72

Using a similar procedure to that described in Example 26, there was obtained (4-amino-2,5-dimethylphenylsulphonyl)nitromethane as a solid, m.p. 116° C. [after recrystallisation from ethanol]; microanalysis, found: C,44.1; H,4.9; N,11.3%; C9H12N2O4S requires: C,44.3; H,4.9; N,11.5%; in 70% yield; starting from (4 acetamido-2,5-dimethylphenylsulphonyl)nitromethane.

EXAMPLE 73

Tetrabutylammonium borohydride (3.85 g, 15 mmol) was added to a solution of (4-acetamido-b 2,6-dimethylphenylsulphonyl)nitromethane (1.43 g, 5 mmol) in dichloromethane (30 ml), and the solution was stirred at reflux for 18 hours. The solvent was removed by evaporation, 2M hydrochloric acid (30 ml) was added to the residue, and the mixture was stirred at reflux for 20 minutes. The solution was then poured into sufficient of an ice-cold saturated solution of sodium hydrogen carbonate, so that the pH of the mixture became 6-7. The mixture was then extracted with ethyl acetate, and the combined extracts were dried (MgSO4). The solvent was removed by evaporation and the resultant yellow oil was purified by flash chromatography on silica (Merck Kieselgel Art. 7736), eluting with dichloromethane, to give (4-(N-ethylamino)-2,6-dimethylphenylsulphonyl)nitromethane as a pale yellow solid (in 58% yield); m.p. 143° C. (after recrystallisation from ethanol); microanalysis, found: C,48.7; H,6.1; N,10.4%; C11H16N2O4S requires: C,48.53; H,5.9; N,10.3%.

EXAMPLE 74

Using a similar procedure to that described in Example 70, but starting from (4-acetamidophenylsulphonyl)-nitromethane, there was obtained 4 (N-ethylaminophenylsulphonyl)nitromethane as a solid (in 40% yield); m.p. 82° C. (after recrystallisation from ethanol); microanalysis, found: C,44.5; H,5.1; N,11.3%; C9H12N2O4S requires: C,44.3; H,4.9; N,11. 5%.

EXAMPLES 75-80

Using a similar procedure to that described in Example 21 but starting from the appropriate sodium sulphinate of formula IV (M=sodium), there were obtained the following compounds of formula I in yields of 20% or less:

| Example | Q | m.p. (°C.) | Recrystallisation solvent(s) |
|---|---|---|---|
| 75 | 4-bromo-2,6-dimethylphenyl | 105-106 | ethyl acetate/hexane |
| 76 | 2,3-dimethylphenyl | 68-70 | ethyl acetate/hexane |
| 77 | 4-bromo-2-methylphenyl | 94-95 | ethyl acetate/hexane |
| 78 | 4-fluoro-2-methylphenyl | 51-52 | ether/hexane |
| 79 | 2,4-dichloro-5-methylphenyl | 121-123 | ethyl acetate/hexane |
| 80 | 2-ethylphenyl | 40-41 | * |

*[Purified by MPLC using dichloromethane/hexane (3:1 v/v)].

The starting material for Example 75, sodium b 4-bromo-2,6-dimethylbenzenesulphinate, was obtained as follows:

A solution of 4-bromo-2,6-dimethylaniline (b 20 g, 100 mmol) in concentrated sulphuric aid (90 ml) was added to cold water (270 ml) with stirring. When the addition was complete, the mixture was cooled to −5° C. and a solution of sodium nitrite (7.8 g, 113 mmol) in water (50 ml) was added. After 30 minutes, sulphur dioxide was bubbled through the reaction mixture, maintaining the bath temperature at −5° C., until an increase in weight of 35 g was obtained. Copper bronze powder (70 g) was then added in portions to the resulting pale brown solution. After vigorous effervescence had ceased, ether (1000 ml) was added and the mixture was allowed to stir for 30 minutes. Insoluble material was then removed by filtration and the organic phase was separated. The aqueous phase was extracted with ether (200×3), and the combined organic phases were dried (MgSO4). The solvent wa removed by evaporation to give 4-bromo-2,6-dimethylbenzenesulphinic acid as a pale brown crystalline solid (15 g).

The acid was converted to its sodium salt by the method described in Example 1, and was used without purification or characterisation.

EXAMPLE 81

Nitromethane (4.6 ml, 82.3 mmol) was added to a stirred solution of sodium hydroxide (7.9 g, 197.5 mmol) in water (50 ml). A solution of sodium 2-bromobenzenesulphinate (20 g, 82.5 mmol) in water (100 ml) was added, followed by dichloromethane (50 ml). The reaction mixture was cooled in an ice bath and a solution of potassium ferricyanide (3 g, 9.1 mmol) in water (20 ml) was added, followed by solid sodium persulphate (12 g, 50.4 mmol). The resultant deep orange solution was allowed to stir for one hour at ambient temperature. Ether (25 ml) was added, followed by urea (5 g), and the pH of the reaction mixture was then adjusted to pH 6 with 20% aqueous acetic acid solution. The organic phase was separated and the aqueous phase was extracted with ether (150 ml×bb 3). The combined organic phases were dried (MgSO4), and the solvent was removed by evaporation. The resultant brown solid was purified by MPLC, eluting with dichloromethane, to give (2-bromophenylsulphonyl)nitromethane as a pale yellow solid (0.197 g), m.p. 74°-76° C.; microanalysis, found: C,29.7; H,2.1; N,4.9%; C7H6BrNO4S requires: C,30.0; H,2.1; N,5.0%.

The necessary sodium sulphinates of formula IV used in Examples 76-81 were prepared by an analogous procedure to that described for the preparation of sodium 4-bromo-2,6-dimethylbenzenesulphinate, but starting from the appropriately substituted anilines.

EXAMPLE 82

Using a similar procedure to that described in Example 21, there was obtained (4-t-butyl-2,6-dimethylphenylsulphonyl)nitromethane as a solid (in 16% yield); m.p. 90°-92° C. (after recrystallisation from hexane);

microanalysis, found: C,54.9; H,6.8; N,5.0%; $C_{13}H_{19}NO_4S$ requires: C,54.7; H,6.7; N,4.9%; starting from 4-t-butyl-2,6-dimethylbenzenesulphonyl chloride, itself obtained by chlorosulphonation of 5-t-butyl-1,3-dimethylbenzene using conventional procedures.

EXAMPLE 83

Using a similar procedure to that described in Example 17, except that the reaction mixture was stirred at 20° C. for 4 hours, there was obtained (2,4-difluorophenylsulphonyl)nitromethane as white needles m.p. 74°–75° C. (purified by recrystallisation from ether/hexane (1:20 v/v); microanalysis, found; C,35.4; H,2.1; N,5.9%; $C_7H_5F_2NO_4S$ requires: C,35.4; H,2.1; N,5.9%; in 33% yield, starting from (2,4-difluorophenylthio)nitromethane [itself isolated as an oil having a satisfactory NMR spectrum (200 MHz, $CDCl_3$); 5.37(s,2H), 6.94(m,2H), 7.57(m,1H), after purification by flash column chromatography on silica (Merck Kieselgel Art 7736) using ethyl acetate/hexane (1:10 v/v)].

EXAMPLE 84

Using assimilar procedure to that described in Example 17, except that the reaction mixture was stirred at 20° C. for 18 hours, there was obtained (4-trifluoromethylphenylsuphonyl)nitromethane as a white solid, m.p. 122°–124° C. (purified by column chromatography on silica (Merck Kieselgel Art. 9385) using ethyl acetate/hexane (1:10 v/v); microanalysis, found: C,35.9; H,2.3; N,5.3%; $C_8H_6F3NO_4S$ requires: C,35.7; H,2.2; N,5.2%; in 27% yield, starting from (4-trifluoromethylphenylthio)nitromethane [itself isolated as an oil having a satisfactory NMR spectrum (200 MHz, $CDCl_3$); 5.52(s,2H), 7.59(d,2H), 7.64(d,2H) after purification by flash column chromatography on silica (Merck Kieselgel Art 7736) using ethyl acetate/hexane 1:10 v/v)].

EXAMPLE 85

The following illustrate representative pharmaceutical dosage forms containing a compound of formula I, or a non-toxic salt thereof, (hereafter "compound X"), [for example, one of the novel compounds exemplified hereinbefore or the known compound (4-bromophenylsulphonyl)nitromethane, or a non-toxic salt thereof], for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium stearate | 1.5 |

| (e) Injection I | (50 mg/ml) |
|---|---|
| Compound X | 5.0% w/v |
| 1 M Sodium hydroxide solution | 15.0% v/v |
| 0.1 M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate EP | 3.6% w/v |
| 0.1 M Sodium hydroxide solution | 15.0% v/v |
| Water for injection to 100% | |

| (g) Injection III | (1 mg/ml, buffered to pH 6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water to injection to 100% | |

CHEMICAL FORMULAE

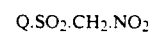  I

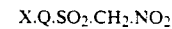  II

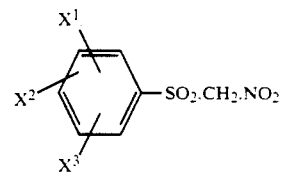  III

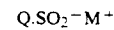  IV

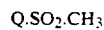  V

  VI

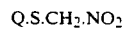  VII

  VIII

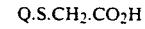  IX

Q.S.CH($NO_2$).$CO_2$H  XI

What is claimed is:

1. A pharmaceutical composition which comprises an active ingredient a nitromethane of the formula I of the structure $Q.SO_2.CH_2.NO_2$ wherein Q is a phenyl ring optionally bearing 1, 2 or 3 substituents which are independently selected from:

hydrogen, halogeno, nitro, hydroxy, amino, alkylamino or dialkylamino of up to 6 carbon atoms, (1-3C)alkanoylamino, (1-6C)alkanoyl, (1-6C)alkyl, (2-6C)alkenyl, (3-6C)alkenyloxy, fluoro(1-4C)alkyl, (1-6C)alkoxy, fluoro(1-4C)alkoxy, hydroxy(1-6C)alkyl, (1-4C) alkoxy(1-4C)alkyl, carbamoyl, alkyl or dialkylcarbamoyl of up to 7 carbon atoms, sulphamoyl, alkyl or dialkylsulphamoyl of up to 6 carbon atoms, (1-6C)alkoxycarbonylamino, (1-6C)alkanesulphonamido, (1-6C)alkyl.S(O)$_n$—, in which n is 1 or 2, phenyl, phenoxy, benzyloxy, benzamido and benzenesulphonamido, the benzene moiety of the last five groups optionally bearing a halogeno, (1-6C) alkyl or (1-6C) alkoxy substituent; or Q bears 4 or 5 substituents independently selected from halogeno, (1-6C)alkyl or (1-6C)alkoxy; or a non-toxic salt of said nitromethane of formula I; together with a pharmaceutically acceptable diluent or carrier, but excluding compositions of compounds of formula I in which Q is unsubstituted or bears a 4-methyl, 4-chloro, 4-fluoro or 4-acetamido substituent and in which the diluent or carrier consists of an alcohol or an alcohol/water mixture.

2. A composition as claimed in claim 1 wherein in the active ingredient of formula I Q is unsubstituted phenyl or phenyl bearing 1, 2 or 3 substituents which may be the same or different and are chosen from: fluoro, chloro, bromo, iodo, nitro, hydroxy, amino, methylamino, ethylamino, propylamino, butylamino, dimethylamino, diethylamino, (methyl)(propyl)amino, formamido, acetamido, propionamido, formyl, acetyl, propionyl, butyryl, methyl, ethyl, propyl, isopropyl, butyl, sec-butyl, t-butyl, vinyl, allyl, 1-propenyl, 2-methyl-2-propenyl, allyloxy, 2-methyl-2-propenyloxy, 3-methyl-b 3-butenyloxy, trifluoromethyl, pentafluoroethyl, 2,2,2-trifluoroethyl, 3,3,3-trifluoropropyl, methoxy, ethoxy, propoxy, isopropoxy, butoxy, t-butoxy, trifluoromethoxy, 2,2,2-trifluoroethoxy, pentafluoroethoxy, hydroxymethyl, 1-hydroxyethyl, 2-hydroxyethyl, 3-hydroxypropyl, 1-methoxyethyl, 2-methoxyethyl, 3-methoxypropyl, methanesulphonamido, ethanesulphonamido, butanesulphonamido, N-methylcarbamoyl, N,N-dimethylcarbamoyl, N-ethylcarbamoyl, N,N-diethylcarbamoyl, N,N-dipropylcarbamoyl, N-methylsulphamoyl, N-ethylsulphamoyl, N-propylsulphamoyl, N-butylsulphamoyl, N,N-dimethylsulphamoyl, N,N-dipropylsulphamoyl, methylsulphinyl, ethylsulphinyl, methylsulphonyl, ethylsulphonyl, phenyl, phenoxy, benzyloxy, benzamido and benzenesulphonamido, any of which last five groups may be unsubstituted or may themselves bear a fluoro, chloro, bromo, methyl, ethyl, methoxy or ethoxy substituent; or the group Q defined above bears 4 or 5 substituents which may be the same or different and chosen from fluoro, chloro, methoxy and methyl.

3. A composition as claimed in claim 1 wherein in the active ingredient of formula I Q is phenyl which is unsubstituted or bears 1, 2 or 3 substituents.

4. A pharmaceutical composition which comprises a compound of the formula II of structure X.Q.SO$_2$.CH$_2$NO$_2$ in which Q is benzene and X is hydrogen or a methyl, fluoro, chloro, bromo or acetamido substituent attached at the 4-position of Q, or a non-toxic salt thereof, together with a pharmaceutically acceptable diluent or carrier.

5. A composition as claimed in claim 1 or 4 which is in a form suitable for oral, topical or parenteral administration.

6. A nitromethane of the formula I of the structure Q.XO$_2$.CH$_2$.NO$_2$, or a non-toxic salt thereof, as defined in claim 1 hereinbefore, but excluding those compounds wherein Q is unsubstituted phenyl and wherein Q is phenyl bearing a 4-halogen, 4-(1-6C)alkyl, 4-(2-6C-)alkenyl, or 4-(1-6C)alkanoylamino substituent, and the alkali metal salts thereof.

7. A compound as claimed in claim 6 wherein Q is:
a) phenyl bearing a single 4-substituent chosen from hydroxy, amino, methylamino, diethylamino, carbamoyl, hydroxymethyl, 1-hydroxyethyl, acetyl, methoxy, ethoxy, butoxy, allyloxy, phenoxy, benzyloxy, benzamido, methylsulphinyl, methylsulphonyl and N,N-diethylsulphamoyl;

b) phenyl bearing a single 3-substituent chosen from fluoro, chloro, bromo, methyl, ethyl, trifluoromethyl, trifluoromethoxy, acetyl, hydroxymethyl and 1-hydroxyethyl;

c) phenyl bearing a single 2-substituent chosen from methyl, ethyl isopropyl, fluoro and chloro;

d) phenyl bearing two substituents which may be the same or different and chosen from fluoro, chloro, methyl, trifluoromethyl, methoxy and acetamido;

e) phenyl bearing three substituents which may be the same or different and are chosen from fluoro, chloro, methyl and acetamido;

f) phenyl bearing four or five fluoro or methyl substituents.

8. A nitromethane of formula III having the structure:

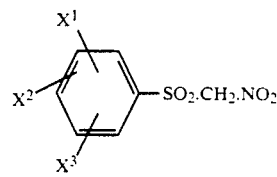

wherein $X^1$ is halogeno, (1-6C)alkyl, (1-6C)alkoxy, (3-6C)alkenyloxy, hydroxy, hydroxy-(1-6C)alkyl or fluoro-(1-4C)alkyl; $X^2$ is hydrogen or one of the values of $X^1$; and $X^3$ is hydrogen or one of the substituents on Q defined in claim 1 or 6, provided that $X^2$ and $X^3$ are not both hydrogen when $X^1$ is 4-halogeno or 4-(1-6C)alkyl; together with the non-toxic salts thereof.

9. A compound as claimed in claim 8 wherein $X^1$ is halogeno or (1-4C)alkyl, $X^2$ is hydrogen or (1-4C)alkyl and $X^3$ is hydrogen, halogeno or (1-4C)alkyl.

10. A compound of the formula I selected from the group consisting of:
(2,4,6-trimethylphenylsulphonyl)nitromethane,
(3-chlorophenylsulphonyl)nitromethane,
(3,4-dichlorophenylsulphonyl)nitromethane,
(2-methylphenylsulphonyl)nitromethane,
(4-chloro-2,5-dimethylphenylsulphonyl)nitromethane,
(2-chloro-3-methylphenylsulphonyl)nitromethane,
(3-chloro-2-methylphenylsulphonyl)nitromethane,
(3-chloro-4-fluorophenylsulphonyl)nitromethane,
and the non-toxic salts thereof.

11. A non-toxic salt as claimed in claim 6 which is a pharmaceutically acceptable salt selected from alkali metal, alkaline earth metal, ammonium and aluminium salts, and salts with organic bases affording physiologically acceptable cations, and for those compounds of formula I which contain an alkylamino or dialkylamino substituent on Q, in addition, physiologically acceptable acid-addition salts with hydrogen halides, sulphuric acid, phosphoric acid, citric acid and maleic acid.

12. A method of inhibiting the enzyme aldose reductase in a warm-blooded animal requiring such treatment which comprises administering to said animal an effective amount of a nitromethane of the formula I, of the structure Q.SO$_2$.CH$_2$.NO$_2$ wherein Q is a phenyl ring optionally bearing 1, 2 or 3 substituents which are independently selected from:

hydrogen, halogeno, nitro, hydroxy, amino, alkylamino or dialkylamino of up to 6 carbon atoms, (1-6C)alkanoylamino, (1-6C)alkanoyl, (1-6C)alkyl, (2-6C)alkenyl, (3-6)alkenyloxy, fluoro(1-4C)alkyl, (1-6C)alkoxy, fluoro(1-4C)alkoxy, hydroxy(1-6C)alkyl, (1-4C)alkoxy(1-4C)alkyl, carbamoyl, alkyl or dialkylcarbamoyl of up to 7 carbon atoms, sulphamoyl, alkyl or dialkylsulphamoyl of up to 6 carbon atoms, (1-6C)alkoxycarbonylamino, (1-6C)alkanesulphonamido, (1-6C)alkyl.S(O)$_n$—, in which n is 1 or 2, phenyl, phenoxy, benzyloxy, benzamido and benzenesulphonamido, the benzene moiety of the last five groups optionally bearing a halogeno, (1-4C)alkyl or (1-4C)alkoxy substituent; or Q bears 4 or 5 substituents independently selected from halogeno, (1-6C)alkyl or (1-6C)alkyl or (1-6C)alkoxy; or a non-toxic salt thereof.

13. A compound according to claim 6 which is (4-amino-2,6-dimethylphenylsulphonyl)nitromethane and the non-toxic salts thereof.

14. A method of inhibiting the enzyme aldose reductase in a warm-blooded animal requiring such treatment, which comprises administering to said animal an effective amount of (4-amino-2,6-dimethylphenylsulphonyl)nitromethane, or a non-toxic salt thereof.

* * * * *